(12) United States Patent
Goldsmith

(10) Patent No.: US 11,215,580 B2
(45) Date of Patent: Jan. 4, 2022

(54) SYSTEM AND METHOD FOR DNA SEQUENCING AND BLOOD CHEMISTRY ANALYSIS

(71) Applicant: Cardea Bio, Inc., San Diego, CA (US)

(72) Inventor: Brett Goldsmith, San Diego, CA (US)

(73) Assignee: Cardea Bio, Inc., San Diego, CA (US)

( * ) Notice: Subject to any disclaimer, the term of this patent is extended or adjusted under 35 U.S.C. 154(b) by 104 days.

(21) Appl. No.: 15/682,449

(22) Filed: Aug. 21, 2017

(65) Prior Publication Data

US 2018/0037952 A1 Feb. 8, 2018

Related U.S. Application Data

(60) Division of application No. 14/684,283, filed on Apr. 10, 2015, now Pat. No. 9,765,395, which is a continuation-in-part of application No. 14/263,954, filed on Apr. 28, 2014, now Pat. No. 9,618,476.

(51) Int. Cl.
| | | |
|---|---|---|
| *G01N 27/414* | (2006.01) | |
| *C12Q 1/6869* | (2018.01) | |
| *C12Q 1/6874* | (2018.01) | |
| *H01L 29/16* | (2006.01) | |

(52) U.S. Cl.
CPC ....... *G01N 27/4145* (2013.01); *C12Q 1/6869* (2013.01); *C12Q 1/6874* (2013.01); *G01N 27/4146* (2013.01); *H01L 29/1606* (2013.01)

(58) Field of Classification Search
CPC .......... G01N 27/4145; G01N 27/4146; C12Q 1/6874
See application file for complete search history.

(56) References Cited

U.S. PATENT DOCUMENTS

| 8,445,945 B2 | 5/2013 | Rothberg et al. |
| 2004/0238379 A1 | 12/2004 | Lindsay et al. |
| 2010/0133510 A1 | 6/2010 | Kim et al. |
| 2010/0248209 A1 | 9/2010 | Datta et al. |
| 2010/0255984 A1 | 10/2010 | Sutter et al. |
| 2010/0327847 A1 | 12/2010 | Leiber et al. |

(Continued)

FOREIGN PATENT DOCUMENTS

| CN | 103323494 A | 9/2013 |
| CN | 104101626 A | 10/2014 |

(Continued)

OTHER PUBLICATIONS

European Patent Office, Supplementary Partial European Search Report, dated Oct. 25, 2017, pp. 1-15.

(Continued)

*Primary Examiner* — Melanie Brown
(74) *Attorney, Agent, or Firm* — Kunzler Bean & Adamson

(57) ABSTRACT

A DNA sequencing and blood chemistry analysis system and method are provided including one or more sensor chips and one or more sample wells, wherein each sample well is configured to form a seal with one of the sensors. The one or more sensor chips may comprise Graphene transistors, and each transistor having an associated sequencing probe. The sensor chips interact with a biological sample introduced into the sample well, wherein changes in the current, transconductance, and resistance of the Graphene transistors are indicative of a DNA binding process. Based on the associated sequencing probes, the DNA sequence present in a biological sample can be identified.

20 Claims, 20 Drawing Sheets

(56) References Cited

U.S. PATENT DOCUMENTS

| | | |
|---|---|---|
| 2011/0165557 A1 | 7/2011 | Ah et al. |
| 2011/0217763 A1 | 9/2011 | Rasooly et al. |
| 2012/0028820 A1* | 2/2012 | Rhodes ................ B82Y 15/00 506/9 |
| 2012/0143027 A1 | 6/2012 | Phillips et al. |
| 2012/0214172 A1 | 8/2012 | Chen et al. |
| 2012/0220053 A1 | 8/2012 | Lee et al. |
| 2013/0089932 A1 | 4/2013 | Wu et al. |
| 2013/0204107 A1 | 8/2013 | Lee et al. |
| 2013/0270521 A1 | 10/2013 | Peng et al. |
| 2014/0042390 A1 | 2/2014 | Gruner et al. |
| 2014/0162390 A1 | 6/2014 | Afzali-Ardakani et al. |
| 2014/0312879 A1 | 10/2014 | Torsi et al. |
| 2015/0038378 A1 | 2/2015 | Cheng et al. |
| 2015/0218094 A1 | 8/2015 | Braunschweig et al. |
| 2015/0276709 A1 | 10/2015 | O'Halloran et al. |
| 2015/0316523 A1 | 11/2015 | Patolsky et al. |
| 2016/0123919 A1* | 5/2016 | Johnson ............. G01N 27/4145 506/38 |
| 2016/0290955 A1 | 10/2016 | Zhong et al. |

FOREIGN PATENT DOCUMENTS

| | | |
|---|---|---|
| KR | 20100107087 A | 10/2010 |
| WO | 2012050646 A2 | 4/2012 |
| WO | 2012112746 A1 | 8/2012 |

OTHER PUBLICATIONS

Nguyen et al. "Graphene Interfaced with Biological Cells: Opportunities and Challenges," The 5 Journal of Physical Chemistry Letters, 2012, vol. 3, pp. 1024-1029.

Mohanty et al. "Graphene-Based Single-Bacterium Resolution Biodevice and DNA Transistor: Interfacing Graphene Derivatives with Nanoscale and Microscale Biocomponents" Nano Lett., Nov. 5, 2008, vol. 8, No. 12, pp. 4469-4476.

Patent Cooperation Treaty, International Search Report for PCT/US2015/026254, dated Jul. 16, 2015, pp. 1-2.

Patent Cooperation Treaty, International Search Report for PCT/US2016/026730, dated Jul. 15, 2016, pp. 1-2.

* cited by examiner

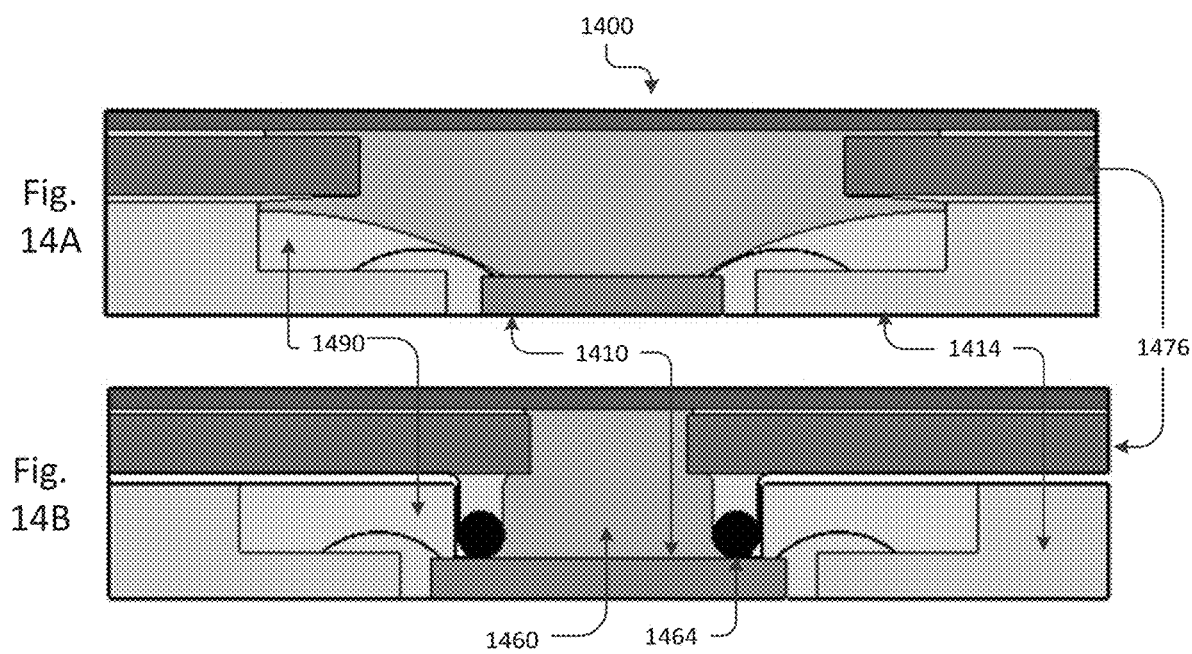

SYSTEM AND METHOD FOR DNA SEQUENCING AND BLOOD CHEMISTRY ANALYSIS

CROSS-REFERENCE TO RELATED APPLICATIONS

This application is a divisional application of U.S. patent application Ser. No. 14/684,283, filed Apr. 10, 2015, which is a continuation-in-part of U.S. patent application Ser. No. 14/263,954, filed Apr. 28, 2014, the contents of which are hereby incorporated by reference in their entireties.

TECHNICAL FIELD

The present disclosure is directed towards electronic biological sample analysis, and more particularly, to electronic DNA and blood chemistry sample analysis.

BACKGROUND

Diagnostic technologies directed towards detecting viral or bacterial infections, or other ailments, within a biological sample generally do not have the sensitivity to directly detect the presence of infectious agents such as a bacteria, virus, or diseased tissue (e.g. cancer) before an immune response occurs. Thus, most diagnostic technologies detect such infections or ailments through detection of antibodies created by a patient's immune system in response to the particular condition. For example, these antibody detection techniques are currently not capable of detecting many diseases within the first month of infection (e.g. Lyme disease). There are laboratory scale analytical and sample treatment techniques capable of detecting markers at an early stage of infection. However, these laboratory techniques require time, expertise and material that prevent common clinical use. One of these laboratory scale sensors is based on direct detection using carbon nanotube devices. Such sensors have been developed in academic labs worldwide. A related material, Graphene, has seen less academic development, but is widely understood to have similar potential use. However, these specialized nanoelectronics lab technologies have yet to be converted into a practical diagnostic systems or methods.

Generally, biological sample analysis to determine the presence of antibodies may be performed on blood or urine samples. Current blood diagnostic systems rely on technologies including enzyme-linked immunoassay (ELISA), gel electrophoresis and blood culture. These are all proven, mature technologies. All three of these tests require significant time to run, from several hours to several days.

ELISA and gel electrophoresis tests generally measure an immune system response to a disease (e.g. the presence of antibodies), rather than presence of the disease itself. Most diagnostic tests, including ELISA and gel electrophoresis tests, require detection of a reporter molecule or molecular label. In these tests, a reporter or amplifier molecule is required to generate a measurable signal.

All of these tests require either significant expertise or very expensive automation equipment to run. This is partly due to the multiple steps and specialized reagents required. For example, ELISA tests are particularly complicated. ELISA tests include coating a measurement well or surface with a copy of a chemical marker created by an infectious agent known as an antigen, incubating a biological sample (e.g. blood, serum, urine, or cerebrospinal fluid), and exposing the measurement well to the biological sample to allow the antibody, if present, to bind to the antigen. The binding process is subject to thermodynamic laws of probability and is not perfect such that some antibodies will bind incorrectly or fail to bind where they should. The ELISA test further includes washing the patient sample from the well, adding a solution with a reporting antibody intended to bind to antibodies bound to the well wall, rinsing the well a second time, and adding a reporting dye to the intended to change colors in the presence of reporting dye. These steps are also subject to variances in binding efficiency and accuracy.

Gel electrophoresis tests are also complicated. In many cases, ELISA is generally preferred for cost and difficulty. Not all infectious agents can be detected by using a blood culture. For example, infection with Borelia burgdoferi is not generally identified via blood culture. The complexity of these tests makes them extremely operator-dependent, creating the possibility for variance in test result accuracy depending on the experience and skill of the operator. Automation could improve accuracy and decrease testing variance, but no such automated solutions are readily available.

Another biological sample analysis technique is based on the polymerase chain reaction (PCR), which clones targeted small fragments of DNA. This is a highly sensitive technique, but also requires either significant expertise or very expensive automated equipment to run properly, and requires several hours for each test.

Another field in which expensive automation equipment and expertise is required is in the field of DNA sequencing. DNA sequencing is the determination of the precise order of the nucleotides within a DNA molecule. By determining the precise order of nucleotides, scientists and researchers are capable of identifying DNA chains associated with particular hereditary diseases and predispositions to develop cancers or other diseases. Equipment for sequencing, however, such as DNA microarray equipment, is expensive and difficult to manufacture.

All of these currently available tests are costly, highly operator dependent, and lack the sensitivity specificity to detect accurately and reliably many diseases, particularly in the disease's early states (e.g. Lyme disease). In addition, DNA sequencing and blood chemistry analysis testing may be improved by increasing sensitivity, as well as reducing the high cost and high operator-dependence of current tests.

SUMMARY OF EMBODIMENTS

The present disclosure is directed towards an electronic biological sample analysis system and method. In particular, the present disclosure is directed towards DNA sequencing using a nanoelectronic circuit by disposing the electronic circuit in the testing device, exposing the testing device to a biological sample, and measuring changes in electrical properties of the electronic circuit system. The changes in electrical properties are analyzed to determine the presence of binding DNA subjugates based on the changes in pH associated with such binding process. This technique can be extraordinarily sensitive, and can be engineered to tailor the sensitivity of the electronic circuit system to obtain desired measurements.

As disclosed herein, an example system for biological sample analysis includes an electronic biological sample sensor system wherein the biological sample sensor system includes one or more sensor chips electronically coupled to an external connector wherein the sensor chips includes one or more transistors. Sequencing probes are associated with the transistors and configured such that if a complimentary DNA sequence is present in a biological sample, such as a suspension containing a DNA sample, the electrical properties of the transistor will change. Based on this change, the DNA sequence in the biological sample may be identified. The sensor system may be enclosed in a case, wherein one or more sample wells are disposed on one side, and each sample well is configured to form a liquid-tight seal with one of the sensor chips.

Also as disclosed herein, an example method for biological sample analysis. A biological sample is introduced into one or more sample wells configured to form a seal with a sensor. The sensor has a plurality of sequencing probes, configured to bind with a complementary sequence of nucleotides in a biological sample. A voltage is applied to the sensor and the output current of the sensor is measured to determine changes in the electrical properties of the sensor chip, such as the transconductance and resistance of the chip, resulting from changes in pH indicative of DNA binding. The DNA sequence of the biological sample is then identified based on the changes in the electrical properties caused by the DNA binding process.

Also as disclosed herein, an example system for biological sample analysis includes a sensing section including one or more sensor chips, wherein each sensor chip comprises one or more transistors and a plurality of sequencing probes; a plate section including one or more biological sample wells, wherein each of the one or more biological sample wells is configured to direct a liquid sample to one of the one or more sensor chips; and a processing section including a processing module.

BRIEF DESCRIPTION OF DRAWINGS

The present disclosure, in accordance with one or more various embodiments, is described in detail with reference to the following figures. The figures are provided for purposes of illustration only and merely depict typical or example embodiments of the disclosure.

FIG. 14A illustrates a side view of a sample chamber from an example biological sample analysis device consistent with embodiments disclosed herein.

FIG. 14B illustrates an alternate side view of a sample chamber from an example biological sample analysis device consistent with embodiments disclosed herein.

The figures are not intended to be exhaustive or to limit the disclosure to the precise form disclosed. It should be understood that the disclosure can be practiced with modification and alteration, and that the disclosure can be limited only by the claims and the equivalents thereof.

DETAILED DESCRIPTION

Embodiments of the present disclosure are directed toward systems and methods for performing biological sample analysis. In some examples, a system for biological sample analysis includes an outer casing, a biological sample delivery system, and an electronic biological sample sensor system. The biological sample delivery system may be configured to deliver a liquid biological sample externally located from the biological sample analysis system to the biological sample sensor system via one or more tubes coupled to a sample chamber, wherein at least one side of the sensor chamber is exposed to a sensor chip in the electronic biological sample sensor system. In several examples, the electronic biological sample sensor system includes the sensor chip and an electronic connector, electrically coupled to the sensor chip, wherein the electronic connector is configured to deliver source-drain voltage and source-gate bias to transistors in the sensor chip, as well as to monitor current flow from the transistors that corresponds to the presence of particular antibodies (e.g. antibodies for Lyme disease) within the biological sample.

Further embodiments of the present disclosure are directed towards systems and methods for performing DNA sequencing and blood chemistry analysis. In some examples, a system for DNA sequencing and blood chemistry analysis includes an outer casing, one or more open-air wells, and an electronic biological sample sensor system. In various embodiments, the electronic biological sample sensor system includes a plurality of sensor chips and an electronic connector, electrically coupled to the plurality of sensor chips, wherein the electronic connecter is configured to deliver source-drain voltage and source-gate bias to transistors in the plurality of sensor chips. Each one of the one or more open-air wells may be configured to deliver a liquid biological sample to one of the plurality of sensor chips.

Figure 1:
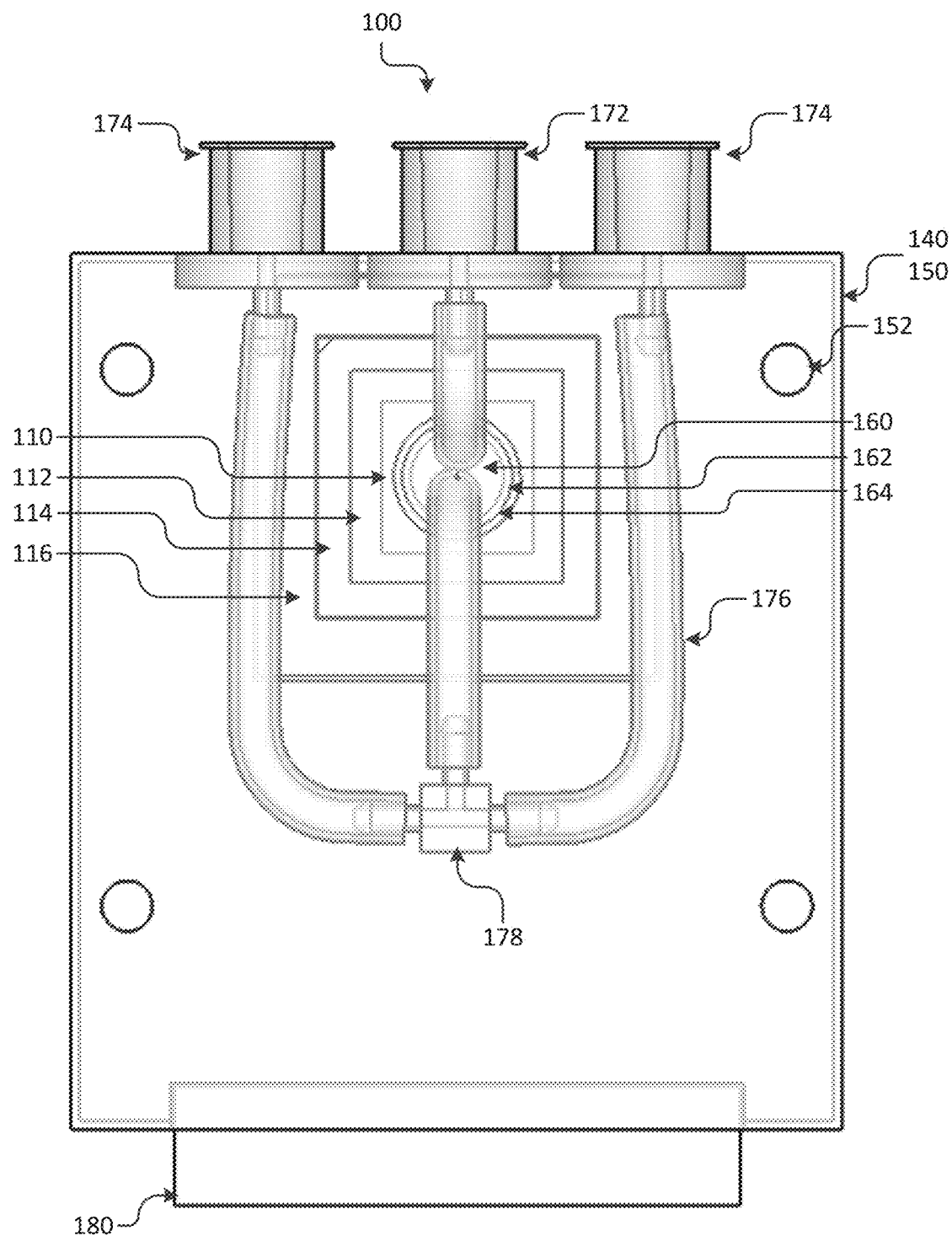
FIG. 1 illustrates a top view of a biological sample analysis device consistent with embodiments disclosed herein.

FIG. 1 illustrates a top view of an example biological sample analysis device. An example biological sample analysis device 100 an outer casing comprising a first cartridge half 140 and a second cartridge half 150 configured to fit together to form a sealed enclosure. First cartridge half 140 and second cartridge half 150 may be aligned and secured together with screws, bolts, tabs, dowels, or other fasteners inserted through mounting holes 152. For example, four mounting holes 152 in first cartridge half 140 may be aligned with four mounting holes 152 in second cartridge half 150 to properly align the two cartridge halves, and then fasteners may be inserted through the holes to secure the halves together.

The external casing of biological sample analysis device 100, in general, is configured to encapsulate an electronic biological sample sensor system enclosed therein. In some examples, the external casing of biological sample analysis device 100 may comprise an outer casing that is a single molded component wherein the molded component comprises plastic, foam, rubber, acrylic, or any other moldable material that is sufficiently watertight. In other examples, the first cartridge half 140 may be hingedly coupled to second cartridge half 150. First cartridge half 140 may also snap fit, press fit, or lock in place when oriented in a closed position with respect to second cartridge half 150 such that the two cartridge halves together form a single cartridge. In some examples, first cartridge half 140 and second cartridge half 150 are aligned using alignment pins or dowels protruding from either the first or the second of the cartridge half, and inserting said alignment pins into alignment holes 152 on the other cartridge half. In one such example, the two cartridge halves may be snap fit, form fit, or press fit together. Other methods of manufacturing a watertight external cartridge casing that are possible as would be known in the art, so long as the external cartridge casing, at least, encloses sample chamber 160 and sensor chip 110.

Still referring to FIG. 1, second cartridge half 150 may further comprise a sensor chip 110, a chip carrier 112, a carrier socket 114, a circuit board 116, and an external connector 180. For example, circuit board 116 may be mounted or form fit inside of second half casing 150 and may be electronically coupled to external connector 180. Circuit board 116 may also support and electronically couple to carrier socket 114, which in turn may support and electronically couple to chip carrier 112. Chip carrier 112 may be configured to physically support and electronically couple to sensor chip 110.

In some examples, sensor chip 110 is a Graphene chip with one or more Graphene transistors, as disclosed herein. The Graphene chip may comprise a plurality of electronic scattering sites located on a top surface of the Graphene chip, wherein each scattering site includes covalently bonded biomarkers that correlate to particular antibodies generated by the human body in reaction to particular infections or diseases (e.g. biomarkers selected for their propensity to bond to antibodies generated by the human body in response to Lyme disease). Further, each scattering site is located on a particular Graphene transistor. The scattering sites are further configured to change the electrical properties of the particular Graphene transistor when the scattering site is exposed to the antibody or antibodies that correlate to the particular bonded biomarker. Accordingly, by applying voltage across the source and drain of each transistor, and properly biasing the source and gate voltage, each Graphene transistor is configured to switch on and/or increase current flow when exposed to a liquid sample containing the antibody or antibodies that correlate to the particular biomarkers bonded to the Graphene transistor's scattering site.

Sensor chip 110 may electrically couple to chip carrier 112. For example, sensor chip 110 may be wire bonded to chip carrier 112. In several embodiments, chip carrier 112 also supports and holds in place sensor chip 110.

Chip carrier 112 may electrically couple to carrier socket 114. In several embodiments, carrier socket 114 supports and holds in place chip carrier 112. Chip carrier 112 may be further configured to snap fit, form fit, or press fit into carrier socket 114 such that electrical leads extending from chip carrier 112 both mechanically and electrically couple to carrier socket 114, but may be mechanically released from carrier socket 114.

Carrier socket 114 may electrically couple to circuit board 116. In several embodiments, circuit board 116 supports and holds in place carrier socket 114. Circuit board 116 may then electrically couple to electrical connector 180. Other electrical and mechanical orientations of sensor chip 110 with respect to circuit board 116 are possible. For example, sensor chip 110 may directly bond to circuit board 116 through a wire bonding, soldering, flip chip solder ball, or other type of electro-mechanical bond as known in the art. In some embodiments, a wire harness or other electric coupling mechanism may facilitate electric coupling of sensor chip 110 with electrical connector 180 such that circuit board 116 is not required.

Still referring to FIG. 1, a biological sample delivery system may be configured to expose sensor chip 110 to a biological sample. The biological sample delivery system may comprise one or more tubes 176, one or more flanges 172 and 174, and sample chamber 160. Flanges 174 and 172 may hydraulically couple to sample chamber 160 through the one or more tubes 176 such that, if a biological sample is introduced through either flange 172 or 174, the biological sample will flow through the tubes 176, into sample chamber 160, and then, if continued pressure is maintained through one of the flanges 172 or 174, the biological sample may be forced out of sample chamber 160 and out of the other flange or flanges 174 or 172. For example, if flanges 174 are input flanges, the flange 172 may act as an exit flange. One of flanges 174 may be used to flush the entire biological sample delivery system with a cleaning solution. Tubes 176 may be hydraulically coupled together with junction 178.

In several examples, sensor chip 110 forms a liquid-tight seal with sample chamber 160. For example, an O-ring 162 may fit within O-ring groove 164 on the outer rim of sample chamber 160, such that when sensor chip 110 is pressed up against sample chamber 160 (e.g. when casing halves 140 and 150 are closed together), O-ring 162 is compressed inside of O-ring groove 164 and against both sample chamber 160 and sensor chip 110, creating a liquid-tight seal.

Figure 2:
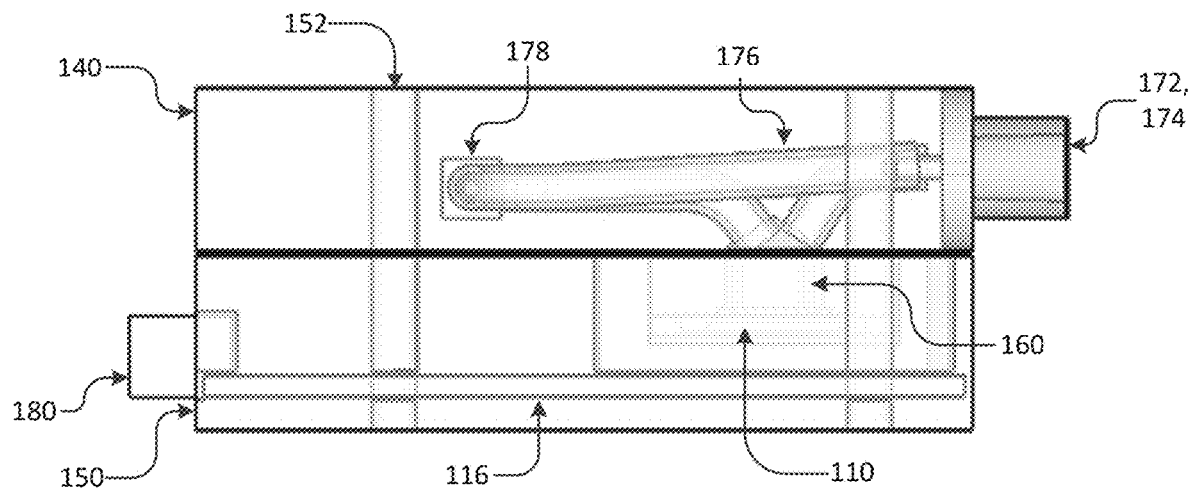
FIG. 2 illustrates a side view of a biological sample analysis device consistent with embodiments disclosed herein.

FIG. 2 illustrates a side view of biological sample analysis device 100. In the non-limiting embodiment illustrated by FIG. 2, casing half 140 is a top half of the casing system and casing half 150 is the bottom half of the casing system. Sample chamber 160 protrudes downward from upper casing half 140 and into bottom casing half 150 when the two halves are configured in the closed position illustrated in FIG. 2. Further, sample chamber 160 is sealed on a bottom side by sensor chip 110 such that, when a biological sample is introduced through flanges 172 and/or 174, it flows through tubes 176, into sample chamber 160, and contacts sensor chip 110.

Figure 3:
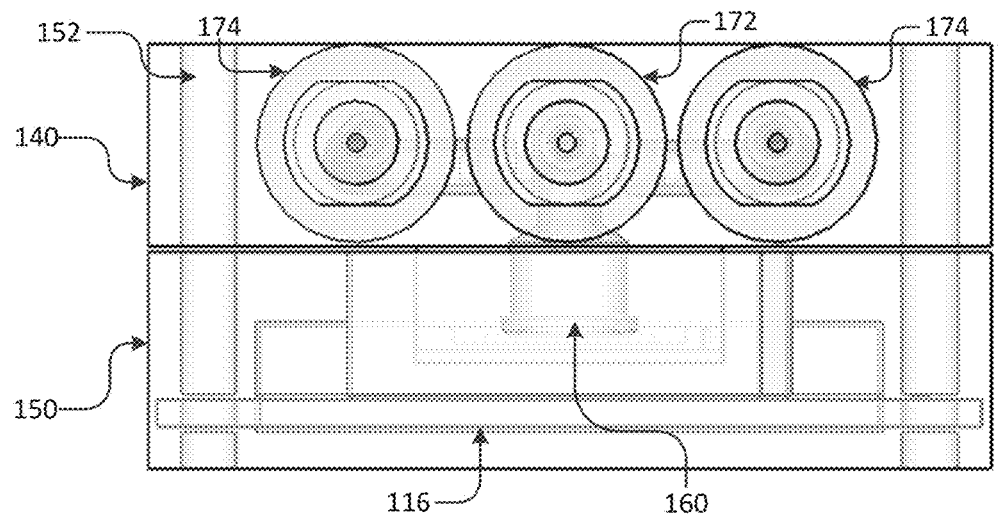
FIG. 3 illustrates a back view of a biological sample analysis device consistent with embodiments disclosed herein.

FIG. 3 illustrates a back view of a biological sample analysis device 100. In the non-limiting example embodiment illustrated by FIG. 3, three sample delivery flanges are located on an external surface of the casing and are configured to hydraulically couple to an external sample deliver system. In some examples, flanges 174 may be input flanges and flange 172 may be an exit flange. For example, one of flanges 174 may be a biological sample input flange, and one of flanges 174 may be a cleaning solution input flange. In other examples, only two flanges may be used, while in some examples, more than three flanges may be used. Other mechanisms for delivering a biological sample to the sensor chip may be used. For example, sensor chip 110 may be dipped in a biological sample stored in a test tube, dewar, cup, catheter bag, or other container. Alternatively, sensor chip 110 may be located within a tube designed to carry the biological sample, or may be configured on a test strip or card and passed directly through the biological sample (e.g. similar to a pregnancy test strip).

Figure 4:
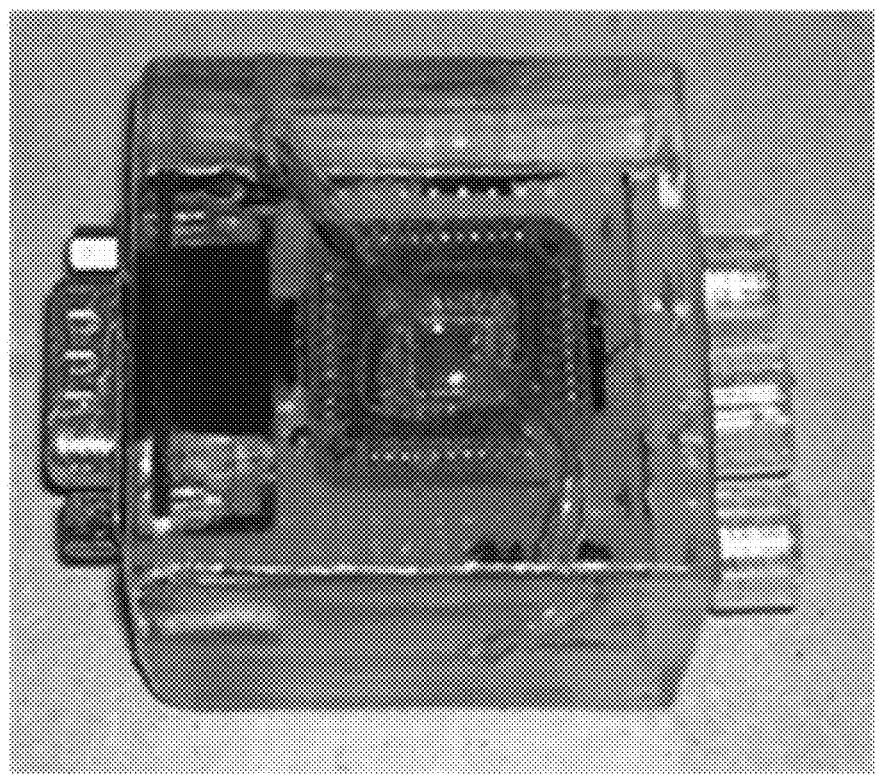
FIG. 4 is a photograph of an example biological sample analysis device consistent with embodiments disclosed herein.

FIG. 4 is a photograph of an example biological sample analysis device. As illustrated by FIG. 4, the casing system may be an acrylic casing or a plastic casing. In other embodiments, the casing system may comprise composite materials, metal, rubber, silicone, glass, resin, or other liquid tight materials as known in the art.

Figure 5:
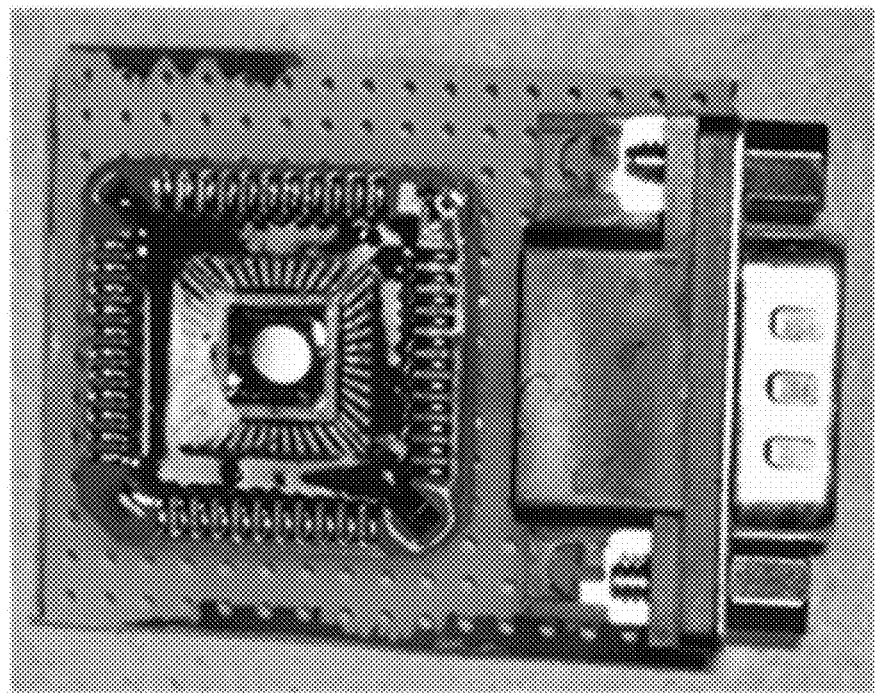
FIG. 5 is a photograph of an electronic biological sample sensor system from an example biological sample analysis device consistent with embodiments disclosed herein.

FIG. 5 is a photograph of an electronic biological sample sensor system from an example biological sample analysis device. As illustrated by FIG. 5, a sensor chip may be wire bonded to a chip carrier, the chip carrier may be coupled to a carrier socket, and the carrier socket may be mounted on a circuit board (e.g. a bread board). The circuit board may then couple to an electronic connector. In some embodiments, the chip carrier is a 44-pin chip carrier. The circuit board may be custom made to electrically couple to the pins from the chip carrier to the connector. In many embodiments, the electronic biological sample sensor system is assembled such that each transistor from the sensor chip completes an electrical circuit through the chip carrier, carrier socket, circuit board, and/or electrical connector. For example, the electrical connector may comprise connector leads for both $V_{DS}$ and $V_{GS}$, to supply drain-source voltage and gate-source bias to each of the transistors on the sensor chip. The electrical connector may further comprise multiple channel leads to monitor and/or measure current flow across each of the transistors independently, such that each channel monitors a different transistor. In some examples, the connector is a sub-D connector.

Figure 6:
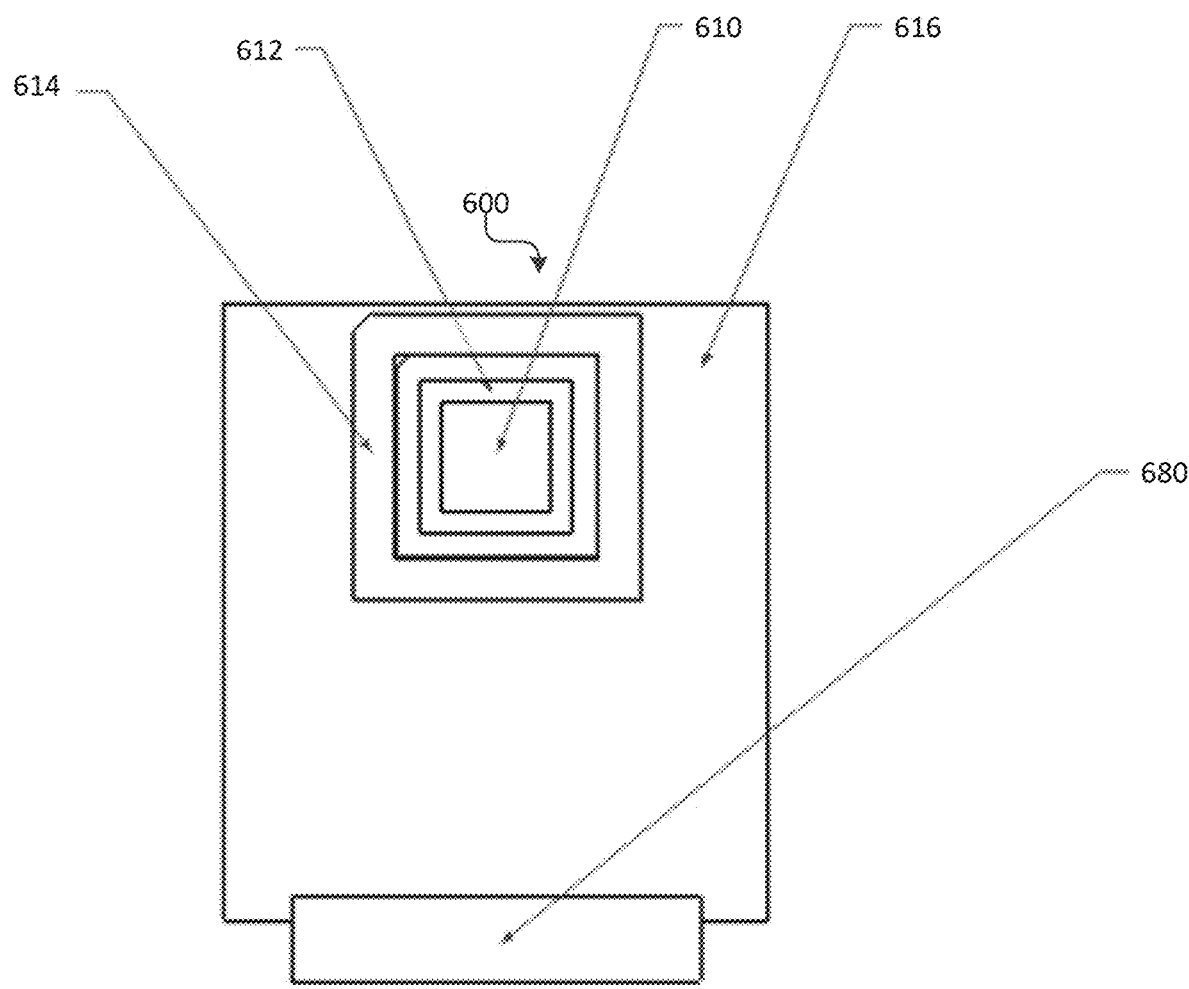
FIG. 6 illustrates a top view of an electronic biological sample sensor system from an example biological sample analysis device consistent with embodiments disclosed herein.

FIG. 6 illustrates a top view of an electronic biological sample sensor system from an example biological sample analysis device. As illustrated, an example electronic biological sample sensor system 600 may comprise sensor chip 610, chip carrier 612, carrier socket 614, circuit board 616, and electrical connector 680. Alternative embodiments may include just sensor chip 610 and electrical connector 680. In some embodiments, an electronic biological sample sensor system is a single integrated circuit comprising one or more Graphene transistors, each transistor being configured to expose the Graphene transistor gates to an external environment (e.g. to a liquid sample resting on a top surface of the Graphene transistor). The electronic biological sample sensor system may further comprise $V_{DS}$ and $V_{GS}$ circuit connections to supply drain-source voltage and gate-source bias to each transistor, as well as at least one electrical channel for monitoring and/or measuring current flow through each transistor.

Figure 7:
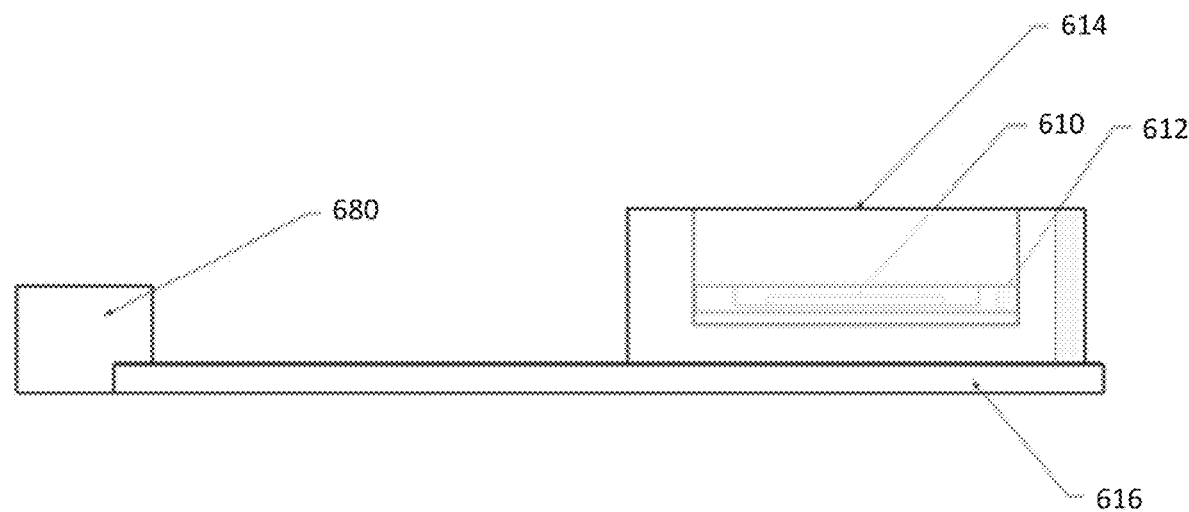
FIG. 7 illustrates a side view of an electronic biological sample sensor system from an example biological sample analysis device consistent with embodiments disclosed herein.

FIG. 7 illustrates a side view of an electronics assembly from an example biological sample analysis device similar to the device illustrated in FIG. 6. Referring to FIG. 7, circuit board 616 may provide electrical connections between electrical connector 680 and sensor chip 610 through chip carrier 612 and carrier socket 614, and may also provide structural support to sensor chip 610, chip carrier 612, and/or carrier socket 614. For example, when sensor chip 610 is bonded to chip carrier 612 and chip carrier 612 is inserted in socket 614, the structural bond between circuit board 616 and carrier socket 612 provides a rigid base for and maintains the structural location of chip carrier 612 and sensor chip 610.

Figure 8:
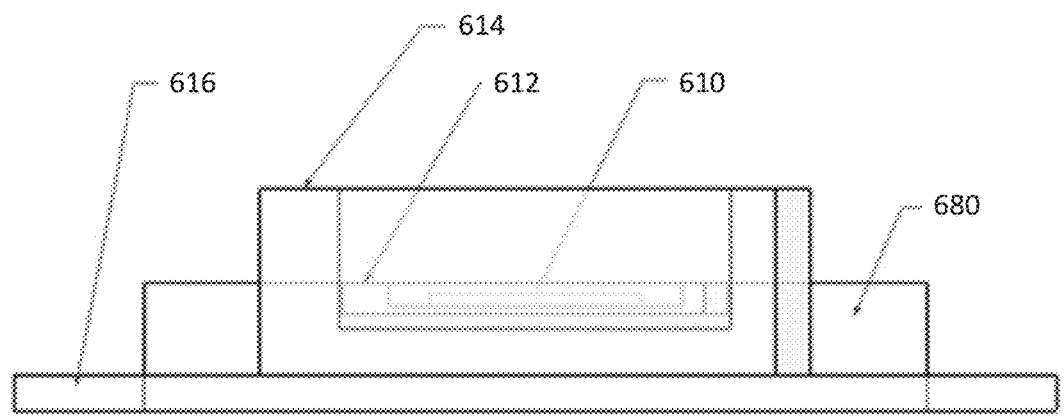
FIG. 8 illustrates a back view of an electronic biological sample sensor system from an example biological sample analysis device consistent with embodiments disclosed herein.

FIG. 8 illustrates a back view of an electronics assembly from an example biological sample analysis device similar to the device illustrated in FIGS. 6 and 7. Referring to FIG. 8, sensor chip 610 may be centrally located with respect to circuit board 616, carrier socket 614, and/or chip carrier 612.

Figure 9:
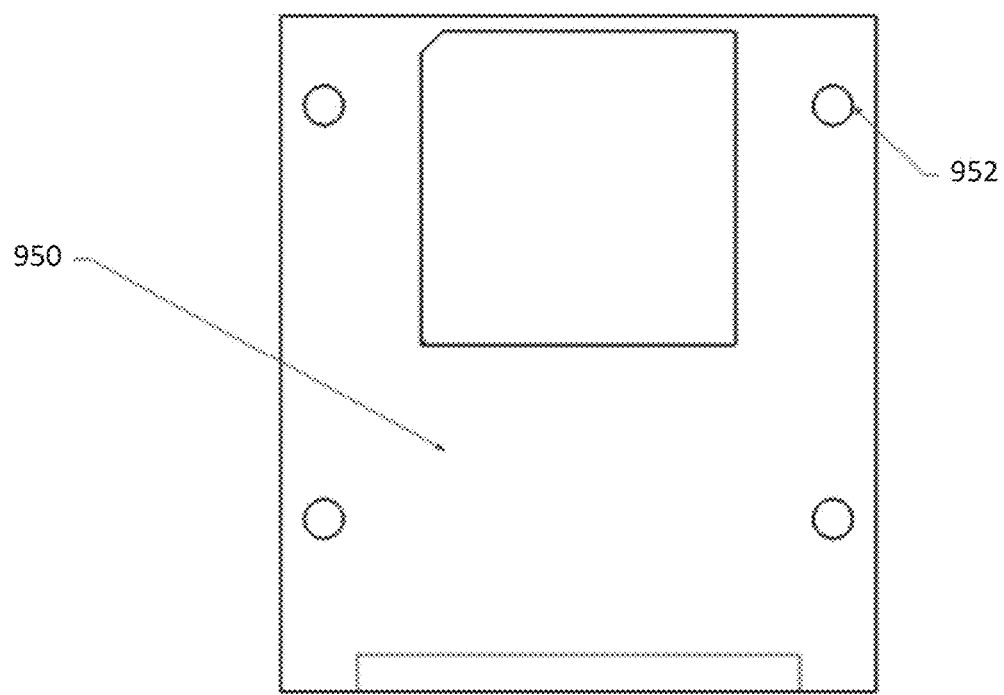
FIG. 9 illustrates a top view of a lower cartridge assembly from an example biological sample analysis device consistent with embodiments disclosed herein.

FIG. 9 illustrates a top view of a lower cartridge assembly from an example biological sample analysis device. Lower cartridge casing 950 may comprise molded or machined plastic, acrylic, glass, ceramic, composite, rubber, metal, or other materials that would be water tight and provide a sterile environment for a biological sample. In some examples, lower cartridge casing 950 comprises thermosetting plastics such as epoxy, polyester or polyurethane or from thermoplastics such as acrylic, polyvinyl chloride or polytetrafluoroethylene (Teflon). Mounting structures 952 may be pins protruding from the casing to mount and align with an upper cartridge assembly, or alternatively, may be holes to accept alignment and/or mounting pins, posts, or screws from the upper cartridge assembly. Other alignment and/or fastening mechanisms may be used to align and secure the upper cartridge assembly with the lower cartridge assembly.

Figure 10:
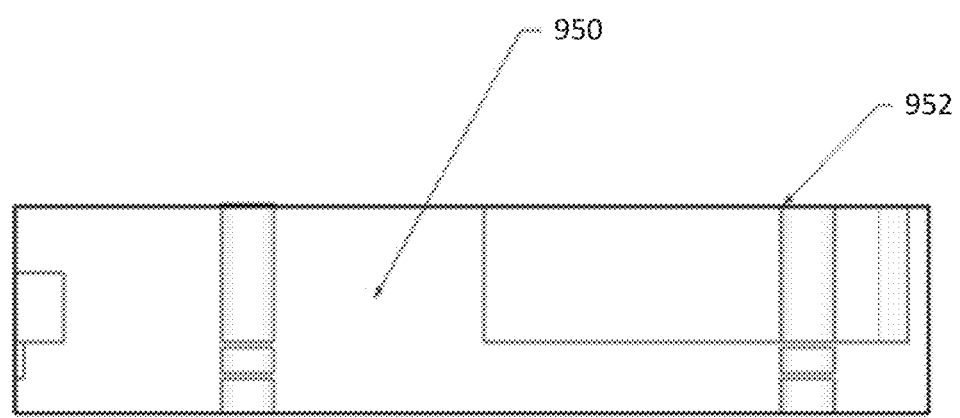
FIG. 10 illustrates a side view of a lower cartridge assembly from an example biological sample analysis device consistent with embodiments disclosed herein.

FIG. 10 illustrates a side view of a lower cartridge assembly from an example biological sample analysis device similar to the device illustrated in FIG. 9. Referring to FIG. 10, example mounting holes 952 may extend vertically through the lower cartridge assembly.

Figure 11:
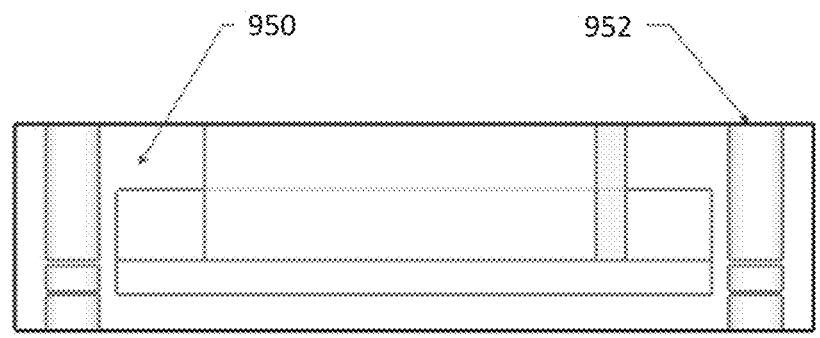
FIG. 11 illustrates a back view of a lower cartridge assembly from an example biological sample analysis device consistent with embodiments disclosed herein.

FIG. 11 illustrates a back view of a lower cartridge assembly from an example biological sample analysis device similar to the device illustrated in FIG. 9. Referring to FIG. 11, openings in casing 950 may be located and configured to accept the electronic biological sample sensor system described in FIGS. 6-8.

Figure 12:
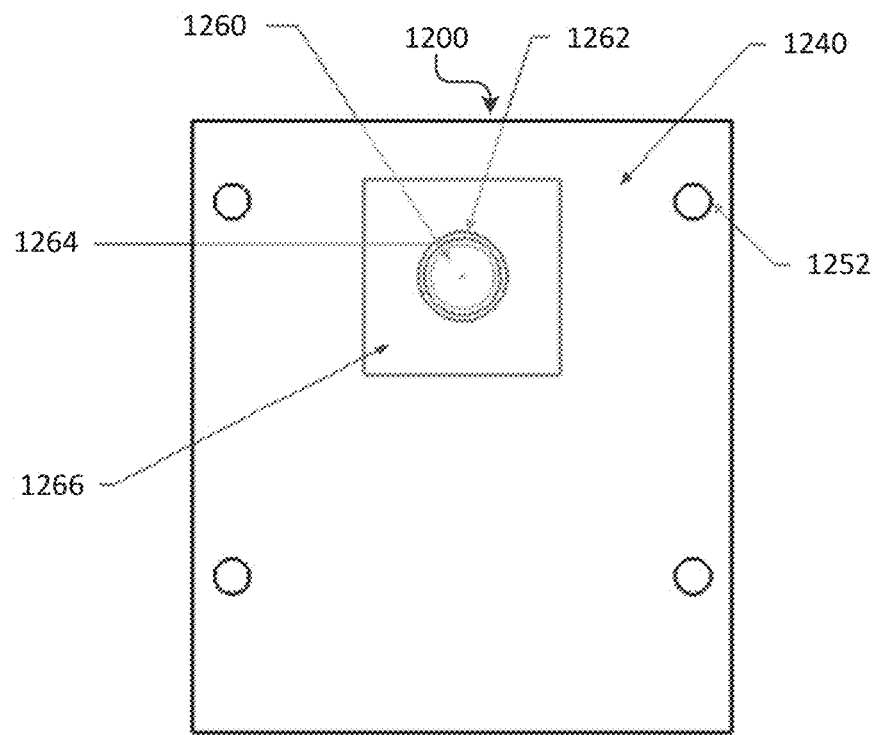
FIG. 12 illustrates an upper view of an upper cartridge assembly from an example biological sample analysis device consistent with embodiments disclosed herein.

FIG. 12 illustrates a top view of an upper cartridge assembly from an example biological sample analysis device. Upper cartridge casing 1240 may comprise molded or machined plastic, acrylic, glass, ceramic, composite, rubber, metal, or other materials that would be water tight and provide a sterile environment for a biological sample. In some examples, upper cartridge casing 950 comprises thermosetting plastics such as epoxy, polyester or polyurethane or from thermoplastics such as acrylic, polyvinyl chloride or polytetrafluoroethylene (Teflon). Mounting structures 1252 may be pins protruding from the casing to mount and align with the lower cartridge assembly, or alternatively, may be holes to accept alignment and/or mounting pins, posts, or screws from the lower cartridge assembly. Other alignment and/or fastening mechanisms may be used to align and secure the upper cartridge assembly with the lower cartridge assembly.

Still referring to FIG. 12, upper cartridge assembly may further comprise biological sample chamber 1260, O-ring groove 1262, O-ring 1264, and/or cartridge body alignment tab 1266. For example, sample chamber 1260 may be configured to hold a liquid biological sample when sealed on a bottom side by the sensor chip from the electronic biological sensor system. O-ring 1264 may be located inside O-ring groove 1262 and configured to form a seal between sample chamber 1260 and the sensor chip when the upper and lower cartridge assemblies are secured together. Cartridge body alignment tab 1266 is shaped to fit inside a similarly shaped socket on the lower cartridge assembly to align the upper and lower cartridge assemblies.

Figure 13A:
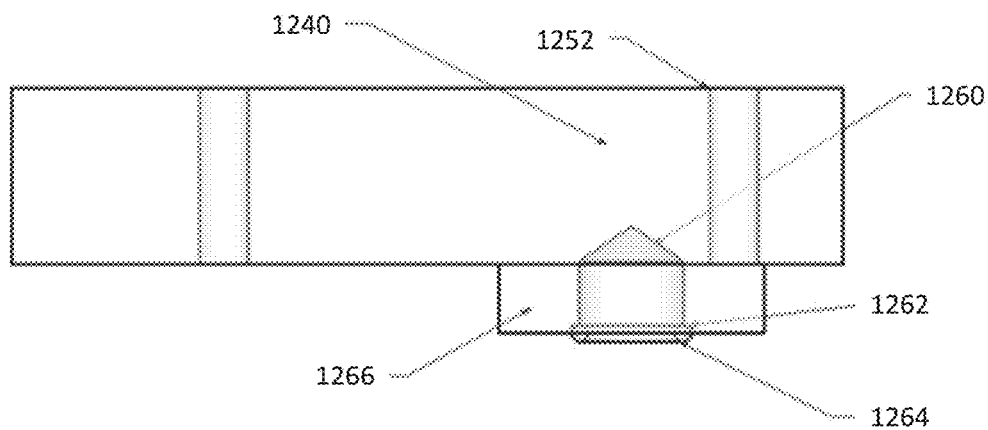
FIG. 13A illustrates a side view of an upper cartridge assembly from an example biological sample analysis device consistent with embodiments disclosed herein.

FIG. 13A illustrates a side view of an upper cartridge assembly from an example biological sample analysis device similar to the device illustrated in FIG. 12. Referring to FIG. 13A, sample chamber 1260 and cartridge body alignment tab 1266 may protrude downward from the upper cartridge assembly.

Figure 13B:
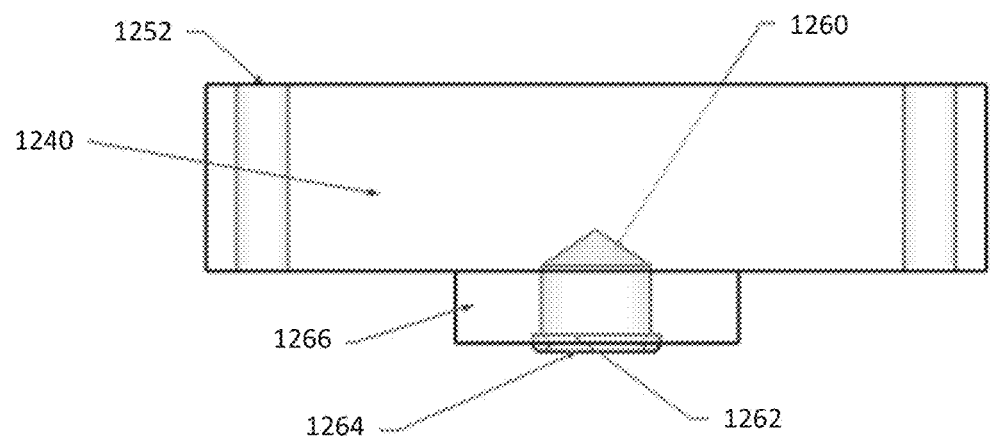
FIG. 13B illustrates a back view of an upper cartridge assembly from an example biological sample analysis device consistent with embodiments disclosed herein.

FIG. 13B illustrates a back view of a top cartridge assembly from an example biological sample analysis device similar to the device illustrated in FIGS. 12 and 13A. Referring to FIG. 13B, sample chamber 1260 and cartridge body alignment tab 1266 may be centrally located within the upper cartridge assembly.

FIG. 14 illustrates a side view of a sample chamber epoxied or molded onto a chip carrier from an example biological sample analysis device clamped to a sensor chip from an example biological sample analysis device. Referring to FIG. 14, sample chamber 1400 comprises a molded solid material (e.g. molded plastic) 1490 configured to hold a liquid biological sample. Sensor chip 1410 is located on a lower side of sample chamber 1400 to complete a seal such that, if a liquid biological sample is placed in the sample chamber, gravity will cause the liquid biological sample to contact a top surface of sensor chip 1410. Sensor chip 1410 may be secured in sample chamber 1400 using epoxy, molded plastic, or another moldable or formable solid material that may be configured to form a liquid-tight and sterile seal with sensor chip 1410. Sensor chip 1410 may also be forced or clamped against O-ring 1464 to form a liquid-tight and sterile seal. As illustrated by FIG. 14, tubing 1476 may be configured to deliver a liquid biological sample into sample chamber 1400.

Figure 15:
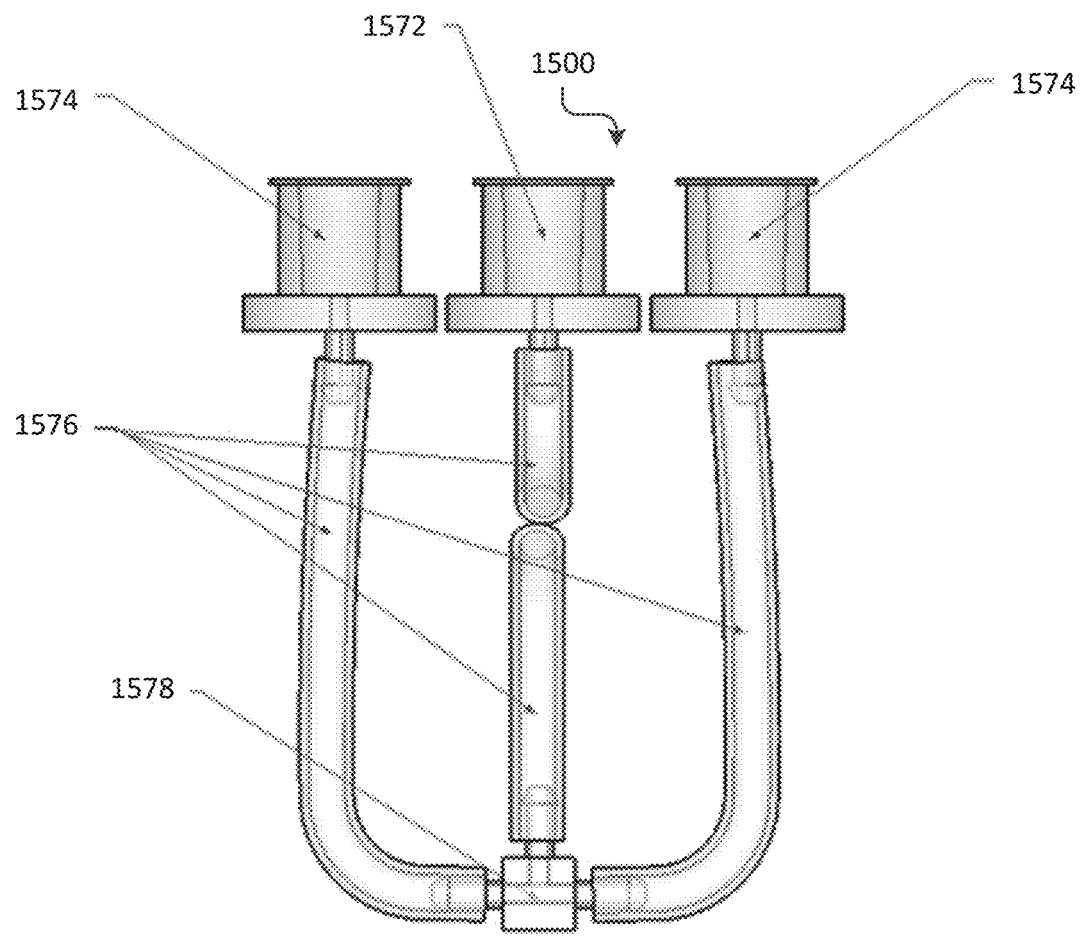
FIG. 15 illustrates a top view of a liquid handling assembly from an example biological sample analysis device consistent with embodiments disclosed herein.

FIG. 15 illustrates a top view of a liquid handling assembly from an example biological sample analysis device. Liquid handling assembly 1500 may comprise one or more tubes 1576 and one or more flanges 1572 and 1574. Flanges 1572 and 1574 are configured to hydraulically connect liquid handling assembly 1500 to an external liquid source. For example, flanges 1574 may accept input from a liquid biological sample source and/or a cleaning source to enable flushing of the liquid handling system with a cleaning solution (e.g. saline). Flange 1572 may be a liquid exhaust flange to enable liquid handling system 1500 to exhaust the biological sample or cleaning solution. Flanges 1572 and 1574 may be Luer fittings, for example. Tubes 1576 may be hydraulically coupled with one or more junction connectors 1578. Liquid handling assembly 1500, and biological sample chamber 1260 illustrated in FIGS. 12-14, may be cleaned with a cleaning solution and/or with steam or chemical sterilization (e.g. bleach, ozone, or hydrogen peroxide).

Figure 16A:
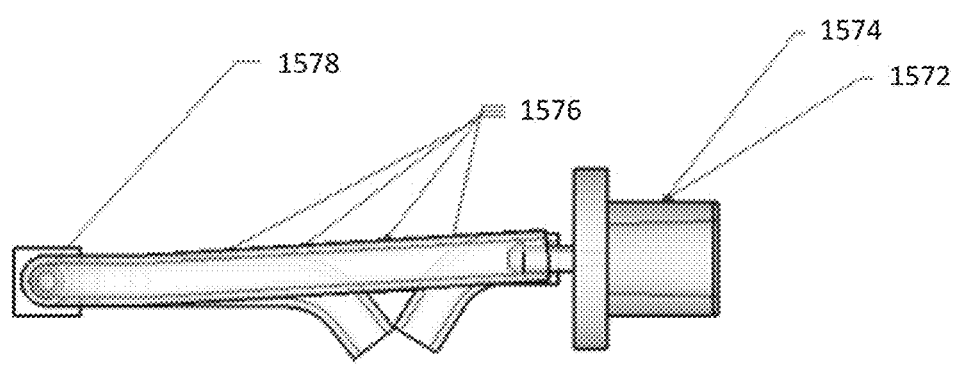
FIG. 16A illustrates a side view of a liquid handling assembly from an example biological sample analysis device consistent with embodiments disclosed herein.
Figure 16B:
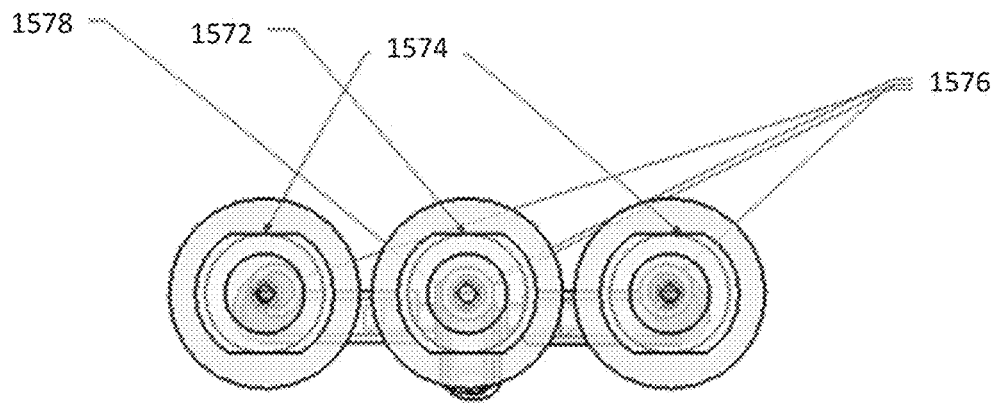
FIG. 16B illustrates a front view of a liquid handling assembly from an example biological sample analysis device consistent with embodiments disclosed herein.

FIG. 16A illustrates a side view and FIG. 16B illustrates a front view of a liquid handling assembly from an example biological sample analysis device from an example biological sample analysis device similar to the liquid handling assembly illustrated in FIG. 15. As illustrated, tube 1576 may couple to flanges 1574 and 1572 with a liquid-tight coupling mechanism such as a burr or form fit coupling. Tubes 1576 also bend downward to deliver a liquid biological sample into the sample chamber.

Figure 17A:
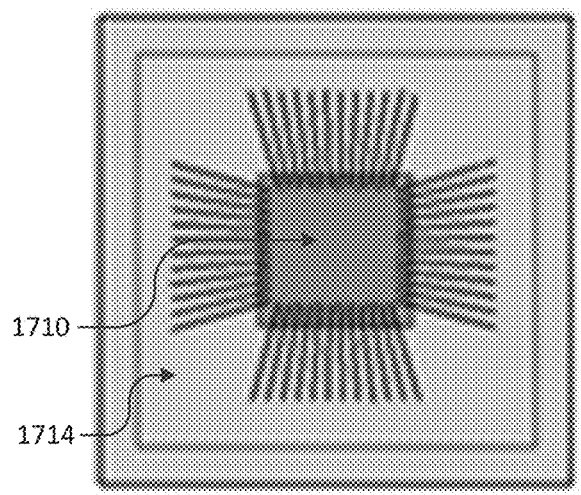
FIG. 17A illustrates a top view of an example biological sample analysis sensor chip wirebonded in a chip carrier consistent with embodiments disclosed herein.
Figure 17B:
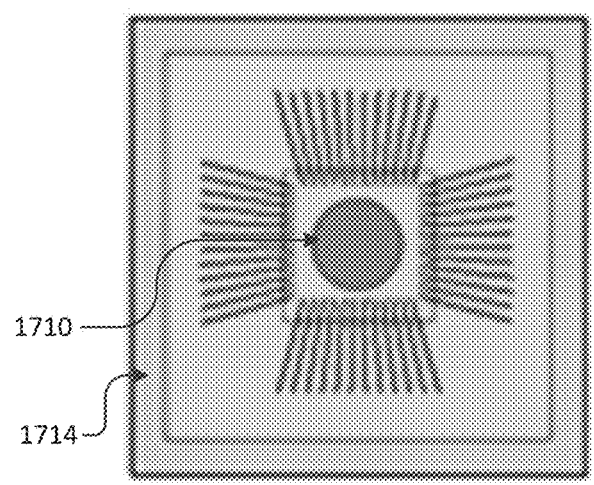
FIG. 17B illustrates a top view of an example biological sample analysis sensor chip covered with a molded plastic cover shaped to form a sample chamber consistent with embodiments disclosed herein.
Figure 17C:
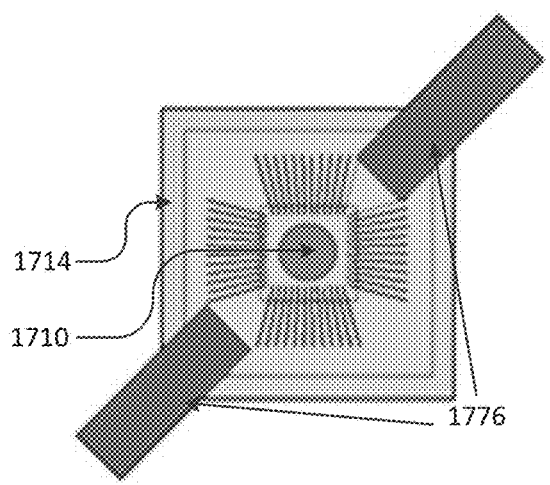
FIG. 17C illustrates a top view of an example biological sample analysis sensor chip covered by a sample chamber that is hydraulically coupled to sample deliver tubing consistent with embodiments disclosed herein.
Figure 17D:
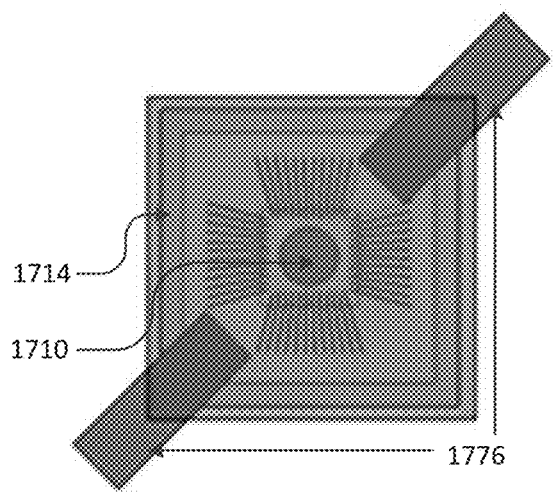
FIG. 17D illustrates a top view of an example biological sample analysis sensor chip covered by a sample chamber and encased in an external casing consistent with embodiments disclosed herein.

FIG. 17A illustrates a top view of an example biological sample analysis sensor chip wirebonded in a chip carrier from an electronic biological sensor system. Sensor chip 1710 may be a Graphene chip with a plurality of Graphene transistors wherein each transistor electrically couples through wire leads to chip carrier 1714. FIG. 17B illustrates a top view of sensor chip 1710 covered with a molded plastic cover shaped to form a sample chamber similar to sample chamber 1400 illustrated in FIG. 14. Accordingly, when a liquid biological sample is introduced into the sample chamber, gravity will cause the biological sample to contact sensor chip 1710. FIG. 17C illustrates a top view of sensor chip 1710, covered with a sample chamber, and hydraulically coupled to tubes 1776 configured to deliver a liquid biological sample into sample chamber 1400. FIG. 17D illustrates a top view sensor chip 1710 covered by a sample chamber and encased in an external casing similar to external casings disclosed in FIGS. 1-4 and 6-14.

Figure 18:
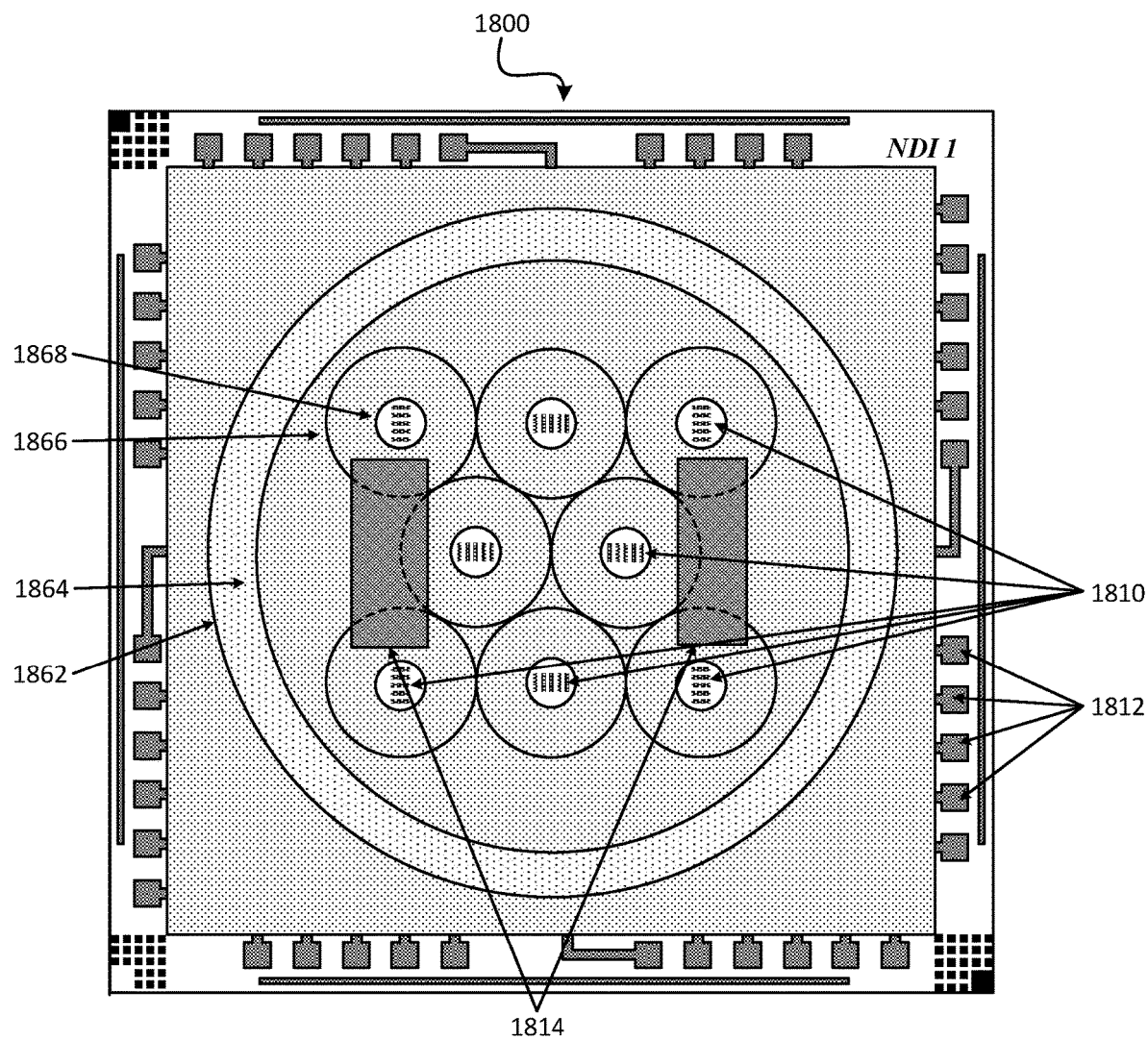
FIG. 18 illustrates a top view of an example biological sample analysis sensor chip consistent with embodiments disclosed herein.

FIG. 18 illustrates a top view of an example biological sample analysis sensor chip as used in an electronic biological sample sensor system. For example, biological sample analysis sensor chip 1800 may comprise one or more transistors 1810. Each transistor 1810 may comprise Graphene. For example, each transistor 1810 may comprise $sp^2$ hybridized Carbon (Csp$^2$) that is a single atomic layer thick, or just a few atomic layers thick. Each Graphene transistor 1810 may further comprise one or more electronic scattering sites, wherein each electronic scattering site comprises Carbon that is sp$^3$ hybridized. Sp$^3$ hybridized Carbon enables covalent bonding with a biomolecule at the Csp$^3$ orbital. The covalently bonded molecules may act as biomarkers wherein predetermined biomarkers will additionally bond to predetermined antibodies generated by a living organism (e.g. a human or a mammal) in response to a particular virus, bacteria, disease, or illness. For example, the Graphene chip may be prepared for chemical functionalization by chemical oxidation with Diazonium salts, Sulfuric Acid, Potassium Permanganate or Hydrogen Peroxide. Antibody attachment may start by linking Carboxylic Acid groups on the Graphene to amine groups on the antibody or linker using 1-Ethyl-3-(3-Dimethylaminopropyl)Carbodiimide (EDC) and N-Hydroxysuccinimide (NETS). A linker molecule may be used when direct attachment to the antibody is not possible. In one example, Streptavidin is used to bind a Biotinylated protein or Nitrotriacetic Acid is used to bind a His-tagged protein. Multiple antibodies can be attached to a single chip by limiting the reaction volume to sufficiently a small drop on top of a group of transistors.

In several embodiments, the Graphene sensor chip may be constructed using a photolithography fabrication process to form Graphene transistors connected to metal contact leads. For example, the Graphene may be a CVD Graphene on a plastic film that is placed on a wafer (e.g. a silicon wafer) and exposed to a solvent (e.g. acetone) to dissolve the plastic and leaving the Graphene on the wafer. The Graphene may then be rinsed (e.g. with isopropyl alcohol, methanol, and/or water) and heated to remove residue. In some examples, the wafer with the Graphene layer is heated for between 30 minutes and four hours. If a shorter time is used, than the wafer with the Graphene layer may be exposed to heat of between 150 degrees C. to 300 degrees C., whereas if a longer heating time is selected, than the wafer with the Graphene layer may be exposed to air at room temperature. Other methods of depositing Graphene on a wafer are possible, including standard material deposition processes as would be known in the art.

One example method for constructing a Graphene sensor chip includes depositing alignment marks and some wiring on a wafer using photolithography, depositing a Graphene layer, and then depositing final wiring using photolithography. Another example method for constructing a Graphene sensor chip includes depositing Graphene and depositing all wiring in a single step. The steps described are non-limiting and may be performed in any order. After the deposition of the Graphene and wires, many examples include dicing the wafers into chips, bonding the chips into chip carriers, and loading the chips onto circuit boards. Several examples further include electrically coupling a socket for the chips to an external electrical connector. In some examples, the bonding of the chip to the chip carrier is a wire bonding process. In some examples, the chip carrier is a 44-pin ceramic or plastic chip carrier, but other chip carrier formats are possible as would be known in the art.

In some examples, the circuit boards are configured such that at least two pins are voltage inputs and the remaining pins are measurement channels. For example, one voltage input may be used to set the drain-source bias on the Graphene transistors ($V_{DS}$) and the other voltage input may be used to set the gate-source bias on the Graphene transistors ($V_{GS}$). The $V_{DS}$ lead may electrically couple to the drain electrode on each Graphene transistor, and the $V_{GS}$ lead may electrically couple to the gate and/or source electrodes of each Graphene transistor and may be used to set the gate/source bias. Measurement channel leads may then electrically couple to individual Graphene transistors to measure current when the Graphene transistor is exposed to a liquid sample. For example, when biomarkers bonded to the Graphene transistor gate are selected for their bonding properties with specific antibodies. When a specific biomarker bonds with the specific antibody, the conductive properties of the Graphene change, causing that particular transistor to switch on, and allowing current to flow to the transistor's source and respective measurement channel. Graphene transistors on any given sensor chip may be configured with a uniform biomarker designed to bond with a uniform antibody (e.g. an antibody for Lyme disease), or multiple biomarkers may be used for the different Graphene transistors, such that a single sensor chip may detect multiple antibodies present in a single liquid sample.

Any biomarker that is known to bond to a particular antibody may be used in the sensor chip to detect the presence of that antibody. The following non-limiting list includes several example diseases and infections with known antibody-to-biomarker relationships:

Autoimmune diseases
Hashimoto's thyroiditis
Hyperthyroidism
Multiple sclerosis
Rheumatoid arthritis
Bacterial infections
*Bacillus anthracis* (anthrax)
*Escherichia coli* (food poisoning)
*Haemophilus influenzae* (bacterial influenza)
*Neisseria gonorrhoeae* (gonorrhea)
*Neisseria meningitides* (meningitis)
*Plasmodium* (malaria)
*Rickettsia prowazekii* (typhus)
*Salmonella enterica* (food poisoning, typhoid)
*Staphylococcus* (food poisoning, staph)
*Streptococcus pneumonia* (pneumonia)
*Treponema pallidum* (syphilis)
Viral infections
Ebola
Epsein-Bar virus
Hepatitis A, B, C, D, E
Herpes simplex virus (cold sore, herpes)
Herpes zoster (chickenpox, shingles)
HIV
Human coronavirus (common cold)
Influenza (common cold)
Norovirus
Rhinovirus (common cold)
Rotavirus
SARS coronavirus
Variola virus (smallpox)
Cancer Markers
Alpha fetoprotein
beta-2-microglobulin
beta-human chorionic gonadotropin
Calcitonin
Cancer antigen 123
Cancer antigen 125
Cancer antigen 15-3
Cancer antigen 19-9
Cancer antigen 27.29
Carcinoembryonic antigen
Chromogranin A
Cytokeratin Human chorionic gonadotropin
Osteopontin
Prostate specific antigen Still referring to FIG. 18, transistors 1810 may be organized and/or located within wells 1868 to concentrate a biological sample over the transistors. Wells 1868 may be formed with well structure 1866 that may comprise capillary tubing plastic, rubber, composite, silicon, or other structural materials as known in the art. Each well 1868 may include one or more transistors 1810, and each sensor chip 1800 may include one or more wells 1868, wherein each well may include a homogeneous biomolecule for detection of a particular antibody. In some examples, wells on the same sensor chip may include different biomolecules such that a single sensor chip may be configured to detect a plurality of antibodies. All of the transistors 1810 and wells 1868 make up an antibody detection surface on sensor chip 1800. As illustrated by FIG. 18, the antibody detection surface may be enclosed within O-ring 1864 and configured to be sealed within a sample chamber with a liquid-tight seal. Bond pads, or leads 1812 electrically couple to the transistors or to reference electrodes 1814 and allow the sensor chip to electrically couple to a chip carrier, carrier socket, circuit board, and/or external electrical connector.

Figure 19:
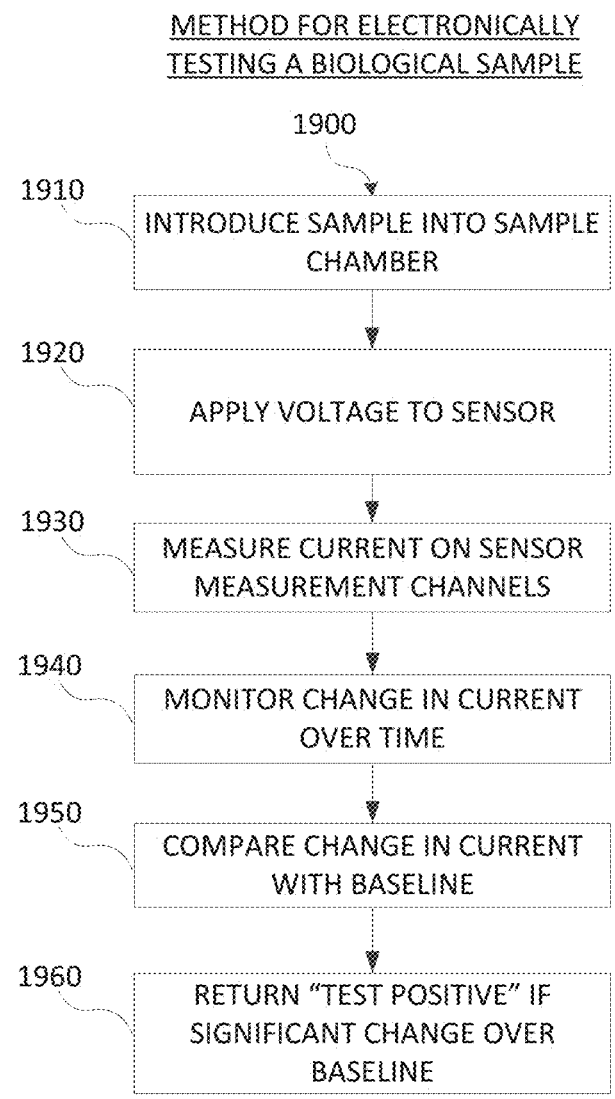
FIG. 19 is a process diagram illustrating a method for electronically testing a biological sample consistent with embodiments disclosed herein.

FIG. 19 is a process diagram illustrating a method for electronically testing a biological sample (e.g. using a biological sample analysis device). A method for electronically testing a biological sample 1900 may include introducing a biological sample into a sample chamber at step 1910. For example, the biological sample may be urine or blood and the sample chamber may be a biological sample chamber and sensor chip similar to embodiments disclosed in FIGS. 1-18. Method 1900 may further include applying a voltage to the sensor chip at step 1920. For example, a voltage may be applied to connector leads electronically coupled to transistors within the sensor chip to supply a drain-source voltage and a gate-source bias. Method 1900 may further include measuring current on sensor measurement channels at step 1930. For example, each sensor measurement channel may be monitored through connector leads electronically coupled to corresponding transistors. Method 1900 may further include monitoring a change in current over time at step 1940, and comparing the change in current with a baseline measurement at step 1950 (e.g. a current measurement taken when the sensor chip was exposed to only saline or another control liquid). Method 1900 may further include returning a "test positive" signal at step 1960 if a threshold change in current over baseline is reached, indicating the presence of an antibody-biomolecule bond at one or more scattering sites as disclosed in FIG. 18.

The steps of measuring current on sensor measurement channels 1930, monitoring changes in current over time 1940, comparing the changes with a baseline measurement 1950, and returning a "test positive" signal may be performed by an electronic biological sample testing module. For example, a biological sample testing module may be a computer module as disclosed in FIG. 25 that includes a processor programmed with one or more computer programs configured to perform the steps disclosed herein. Other steps of method 1900 may be similarly performed by a computer module.

Figure 20:
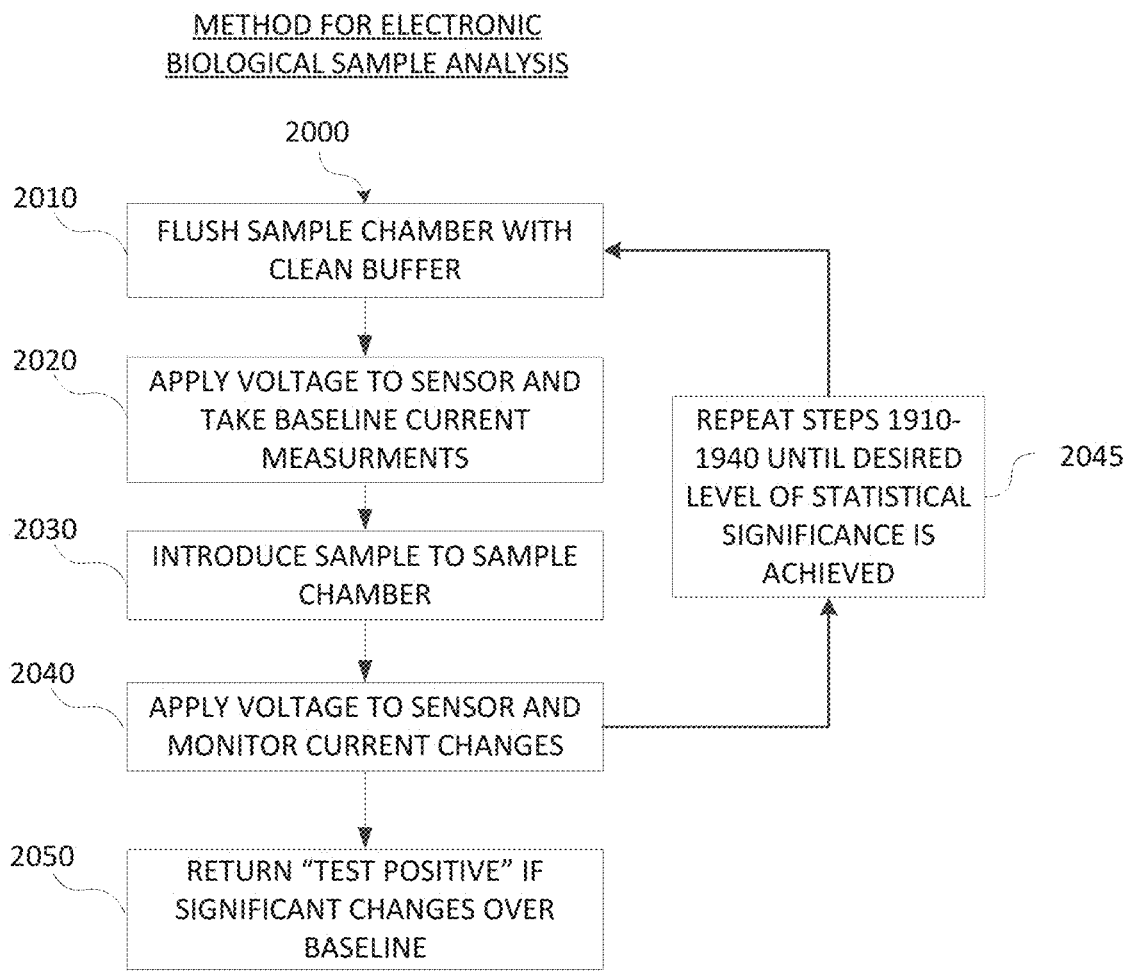
FIG. 20 is a process diagram illustrating a method for electronic biological sample analysis consistent with embodiments disclosed herein.

FIG. 20 is a process diagram illustrating a method for electronic biological sample analysis. A method for electronic biological sample analysis 2000 includes flushing a sample chamber with a clean buffer at step 2010. For example, the sample chamber may be a biological sample chamber similar to embodiments disclosed herein and the clean buffer may be a saline solution or other sterile solution as known in the art. Method 2000 further includes applying voltage to an electronic biological sample sensor system at step 2020. For example, voltage may be applied across the source-drain and source-gate of transistors in a sensor chip. Method 2000 further includes introducing a sample to the sample chamber at step 2030, applying a voltage to the sensor, and monitoring current changes at step 2030. The applied voltage will cause current to vary from a baseline if the biological sample includes antibodies that correspond to biomolecules bonded to scattering sites in the sensor chip transistors. Steps 1910 through 1940 may be repeated multiple times at step 2045 to increase statistical significance of the measurements. Method 2000 may further include returning a "test positive" signal at step 2050 if the average change in current over baseline exceeds a predetermined threshold level. The steps disclosed in method 2000 may be performed by an electronic biological sample testing module. For example, a biological sample testing module may be a computer module as disclosed in FIG. 25 that includes a processor programmed with one or more computer programs configured to perform the steps disclosed herein.

In some examples, all of the applied and measured voltages are referenced to a common ground. A single device measurement may include applying a voltage (e.g between 0.1V and 1V) to the drain of all of the Graphene transistors (VDS) and a voltage (e.g between 1V and 1V) to the liquid in the sensing chamber (VGS). The resulting liquid voltage (VREF) can be monitored through a reference electrode 1814. The electrical baseline of each of the sensors on the chip can be measured by recording the current on all of the sensor measurement channels when VREF is 0V. VGS can be controlled such that if VREF changes up or down (e.g in a range from −1V to 1V) while holding VDS steady. The current can be measured on all of the sensor measurement channels. For each measurement channel, the resulting data, when considered with a Y-axis of current and an X-axis VREF, can be fitted with a line. The slope and X-axis intercept of the line can be calculated where the electrical baseline current, slope, and intercept of the fit line form three data points in a measurement vector for each sensor in a device measurement. To increase statistical significance, a device measurement can be repeated multiple times (e.g. 3 to 5 times) to obtain an average value and statistical variance for the measurement vector for each sensor. This process can be automated using a computer module as disclosed herein.

In some examples, a method for electronic biological sample analysis includes connecting a system for electronic biological sample analysis to an electrical system, flushing the system for electronic biological sample analysis with clean serum or buffer, and measuring a baseline device measurement to obtain a baseline set of measurement vectors. The method may further include injecting a biological sample into the system and measuring a device measurement at regular intervals over an incubation period (e.g. every minute for 10, 20, or 30 minutes). The method may further include flushing the system with clean serum or buffer and measuring a device measurement at a regular interval (e.g. every minute for 1, 5, or 10 minutes). The system may then be flushed with clean serum or buffer again and repeating measuring a device measurement at a regular interval. The method may further include comparing the measurement vectors before, during, and after exposing the system to the biological sample and analyzing the date for a significant change in the measurement vector for many similarly functionalized sensors indicating a binding event, which can be reported as a positive identification.

Figure 21:
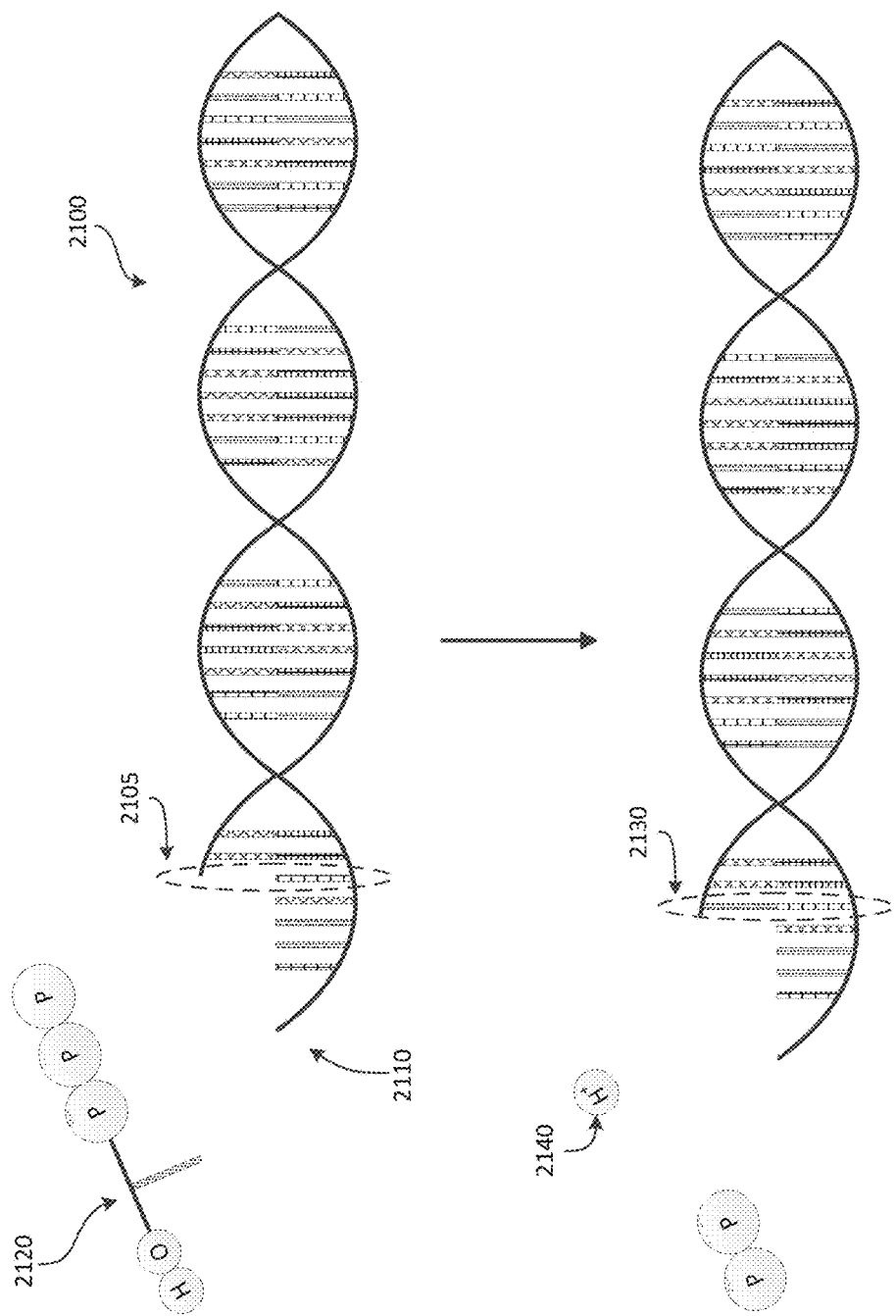
FIG. 21 is an example diagram illustrating the process of binding of subjugate bases of DNA.

The technology of the present disclosure is applicable to not only infection and disease detection, but for other analysis as well. One such type of analysis is DNA sequencing. When subjugate bases of DNA (or RNA) bind, the binding process releases ions into the surrounding suspension. FIG. 21 illustrates an example of the binding process. As illustrated, a DNA chain 2100 is shown with subjugate base pairs. At one end 2110, only one side of the double helix formation is present, with unpaired bases. Binding occurs in the presence of a sequencing probe 2120—shown in FIG. 21 as deoxyribose nucleoside triphosphate (dNTP). A sequencing probe is a fragment of DNA (or RNA in the sequencing of DNA) used to detect the presence of nucleotide sequences that are complimentary to the sequence of the sequencing probe. If the dNTP compliments the next exposed base (illustrated in area 2105), binding occurs and a subjugate base pair is created (illustrated in area 2130). The release of a hydrogen ion results in a change in the local pH of the suspension. By knowing the dNTP being introduced into the suspension, it is possible to determine which base—adenine, thymine, guanine, or cytosine—was exposed and the precise structure of the strand. If a chain of the same exposed base is present (i.e., more than one of the same base is found consecutively on a single-strand of the DNA molecule), more ions will be released, resulting in a greater change in the pH of the suspension. By measuring the change in the electrical properties of transistors caused by changes in pH, it is possible to identify the DNA sequence present in the suspension. Some current DNA sequencing tools employ a silicon transistor pH meter, such as ion-sensitive field-effect transistor (ISFET), to identify changes in the local pH level indicative of DNA binding. The biological sample analysis sensor chip discussed above is exceptionally suited for such DNA testing.

Figure 22:
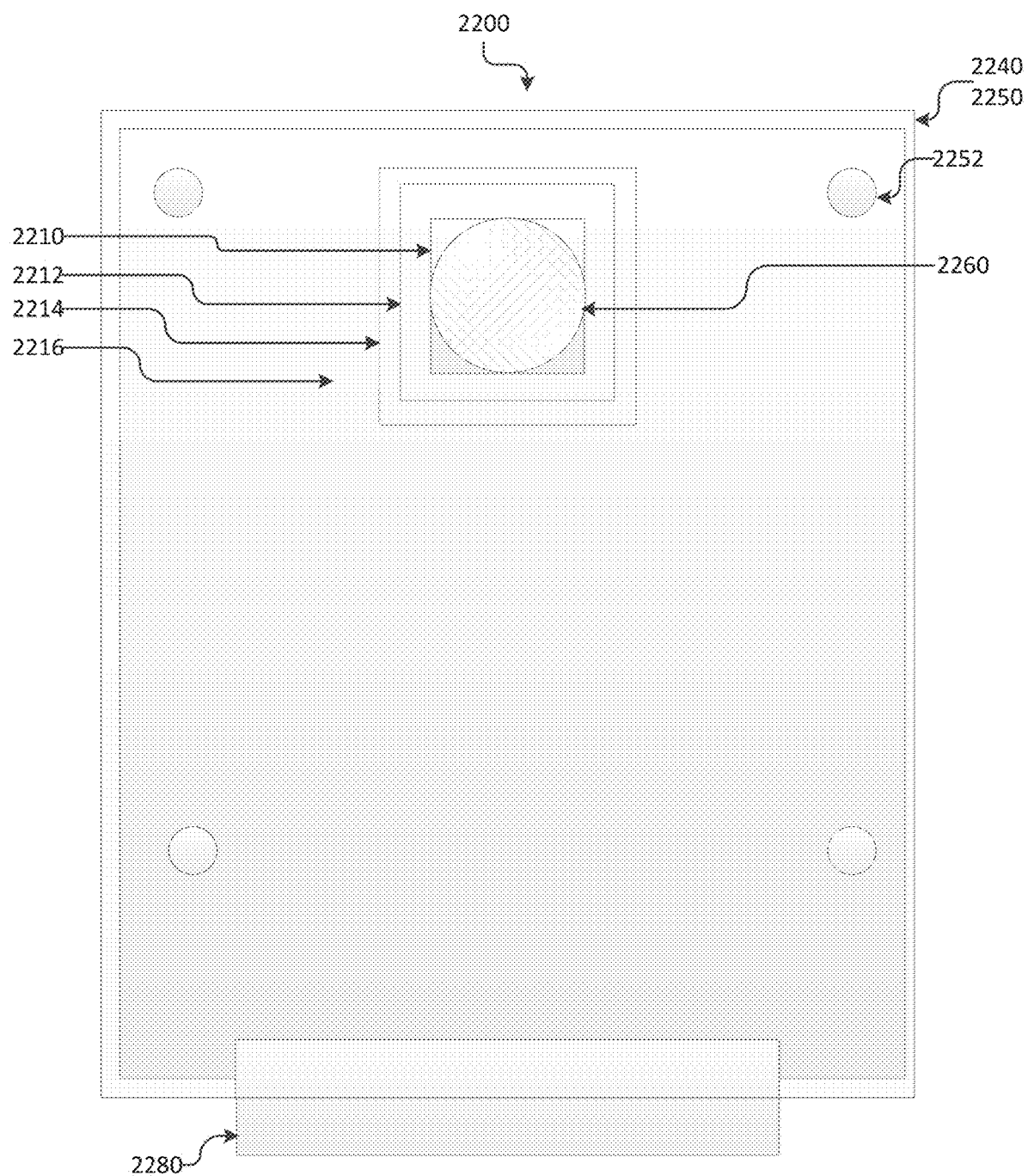
FIG. 22 illustrates a top view of an example DNA sequencing device consistent with embodiments disclosed herein.

FIG. 22 illustrates an example DNA sequencing device 2200 in accordance with the present disclosure. The DNA sequencing device 2200 is substantially similar to the biological sample analysis device described above with respect to FIGS. 1-18. The DNA sequencing device 2200 includes a first cartridge half 2240 and a second cartridge half 2250. The first cartridge half 2240 and the second cartridge half 22502250 may be attached in a manner similar to the biological sample analysis device 100 discussed above with respect to FIG. 1.

As shown in FIG. 22, the first cartridge half 2240 includes an open-air well 2260. In various embodiments, a plurality of open-air wells 2260 may be included in the first cartridge half 2240. In some embodiments, ninety-six (96) open-air wells 2260 may be included in the first cartridge half 2240, similar to standard DNA sequencing plates. The open-air well 2260 serves the same function as the sample chamber 160 discussed above in FIG. 1. The bottom of the open-air wells 2260 are aligned with the sensor chips 2210 such that the open-air wells 2260 are in fluidic communication with the sensor chips 2210 to direct a suspension containing DNA molecules to the sensor chip 2210. A suspension is a liquid solution containing a DNA sample, for example cellular material from a cheek swab. In some embodiments, open-air well 2260 may include an O-ring groove on its outer rim, allowing a liquid-tight seal to form with the sensor chip 2210, similar to the seal discussed above with respect to FIG. 1. In various embodiments, a gasket may be placed in between the open-air wells 2260 and the sensor chips 2210 to seal the open-air wells 2260 and prevent the suspension from seeping into the rest of the DNA sequencing device 2200. In some embodiments, a cover (not pictured) may be included on the first cartridge half 2240. The cover may be configured to enclose the one or more open-air wells 2260 such that no liquid escapes if the DNA sequencing device 2200 is moved.

Still referring to FIG. 22, the second cartridge half 2250 may include a sensor chip 2210, a chip carrier 2212, a carrier socket 2214, a circuit board 2216, and an external connector 2280. For example, circuit board 2216 may be mounted or form fit inside of the second cartridge half 2250 and may be electronically coupled to external connector 2280. Circuit board 2216 may also support and electronically couple to carrier socket 2214, which in turn may support and electronically couple to chip carrier 2212. Chip carrier 2212 may be configured to physically support and electronically couple to sensor chip 2210. In various embodiments, the electrical connector 2280 may be coupled to an amp meter, voltmeter, multi-meter, or another external measurement device for monitoring the change in current or voltage of the transistors. In some embodiments, the electrical connector 2280 may be coupled to a computing device designed to measure current and voltage changes in the transistors due to changes in pH. In some embodiments, the electrical connector 2280 may both provide electricity to the circuit board 2216 and output signals to a device for monitoring, such as a computing device.

Where a plurality of open-air wells are included in the first cartridge half 2140, additional sensor chips 2210 may be required. In such embodiments, the circuit board 2216 may include a plurality of sensor chips 2210, chip carriers 2212, and carrier sockets 2214. Each sensor chip 2210 corresponds to one of the open-air wells 2260 included in the first cartridge half 2240. As discussed above, each sensor chip 2210 is configured to form a liquid-tight seal with one of the open-air wells 2260.

In various embodiments, sensor chip 2210 may be a Graphene chip with one or more Graphene transistors, similar to the Graphene chip discussed above in regards to FIGS. 17-18. Unlike traditional silicon transistors, Graphene does not oxidize in air, is extremely chemically inert, and thermally stable without the need for disposing protective layers on the Graphene. Accordingly, less material is necessary to construct the Graphene chip, and the Graphene chip may be placed directly in contact with the sensing environment.

The Graphene chip used as the sensor chip 2210 may comprise a plurality of electronic scattering sites, with each scattering site located on a particular Graphene transistor. Sequencing probes may be associated with each scattering site and Graphene transistor. In various embodiments, each scattering site may include covalently bonded sequencing probes that are complimentary to specific nucleotide sequences in the suspension. The sequencing probe may be bonded to the Graphene using a linker such as EDC and NHS, discussed above with regards to FIG. 18. In some embodiments, the sequencing probes may not be covalently bonded to the scattering sites, but instead immobilized through bonding to a structure directly adjacent to the Graphene transistor. For example, an immobilization layer of hydrogel or other adherent may be disposed on the Graphene chip 2210, and the sequencing probes may be disposed on the immobilization layer. Sensor chips capable of sequencing all possible base pair possibilities in accordance with the present disclosure can be constructed using high end electronics fabrication techniques, such as the photolithography fabrication process discussed above with regards to FIG. 18.

In various embodiments, the sensitivity of the sensor chip 2210 may be tailored by employing a similar protein binding method discussed above with respect to FIG. 18. Through tailoring the sensitivity of the sensor chip 2210, the DNA sequencing device 2200 may be optimized for a particular pH range. In various embodiments, the voltage shift measurements described above may be used. In some embodiments, the suspension itself may be optimized for a more sensitive reading by selecting solutions that interact more closely with the sensor chip 2210.

In various embodiments, additional calculations may be used to determine the effect of pH change and, accordingly, conduct DNA sequencing. Due to the unique properties of the Graphene used in creating the sensor chip 2210, the effects of pH changes on Graphene are more complex than those seen with typical semiconductor sensors, such as the ISFET. This complexity arises from the fact that the sensor chip 2210 is in direct contact with the sensing environment. In addition, the unique electronic structure of Graphene also contributes to the complexity. Graphene acts as a bipolar transistor, showing electronic characteristics of both n-type and p-type semiconductors. In some embodiments, changes in the transconductance of the Graphene may be used to determine the pH change. Transconductance is the ratio of the current variation at an output to the voltage variation at an input. The transconductance of a transistor is different at different pH levels. In some embodiments, changes in the resistance of the Graphene may be used. In other embodiments, a combination of one or more of the changes in current, transconductance, or resistance due to changes in pH may be used to identify the DNA sequence present in a suspension.

Figure 23:
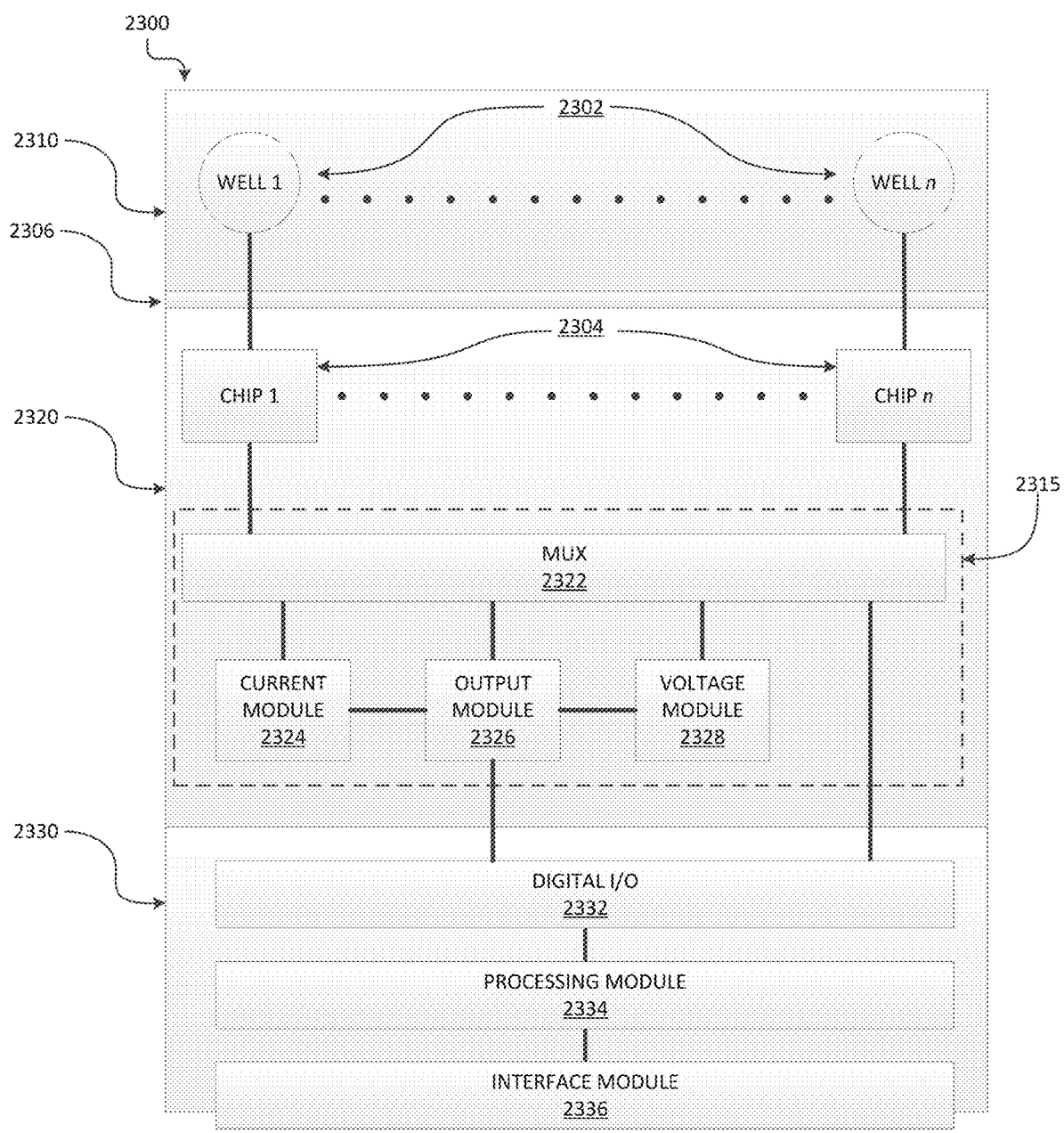
FIG. 23 is a block diagram illustrating another example DNA sequencing device consistent with embodiments disclosed herein.

In various embodiments, it may be beneficial to include some additional processing functionality within the DNA sequencing device itself. FIG. 23 is a block diagram illustrating another example DNA sequencing device 2300 in accordance with the present disclosure. As shown in FIG. 23, the DNA sequencing device 2300 includes a plate section 2310, which includes one or more open-air wells 2302, similar to the open-air wells 2260 described above with regards to FIG. 22. In some embodiments, the plate section 2310 may include ninety-six (96) open-air wells, similar to standard DNA sequencing plates. In some embodiments, the plate section 2310 may include a cover to seal the open-air wells 2302. In various embodiments, the cover may be attached to the plate section 2310 permanently. In other embodiments, the cover may be removable from the plate section 2310. In some embodiments, the cover may comprise individual strips configured to seal one or more open-air wells 2302 within a single column or row. In some embodiments, the plate section 2310 may be removable from the DNA sequencing device 2300. By removing the plate section 2310, cleaning the open-air wells 2302 and the sensor chips 2304 may be accomplished easier. In addition, if the plate section 2310 was to be damaged, but the rest of the device was unaffected, a user may be able to swap out an undamaged plate section for the damages section.

Each of the one or more open-air wells 2302 is configured to sit on top of a sensor chip 2304 embodied in a sensing section 2320. When situated on top of one of the sensor chips 2304, a suspension containing a DNA strand may be directed into the open-air well 2302 and the suspension can contact the sensor chip 2304, similar to the configuration discussed above with regards to FIG. 22. A liquid-tight seal 2306 is formed between each open-air well 2302 and sensor chip 2304. This liquid-tight seal 2306 may be formed in a similar manner as the seal discussed above with regards to FIG. 22. As configured, each sensor chip 2304 can sense changes in current and resistance in the suspension directed into the open-air well 2302 when a nucleotide sequence in the DNA is present that is complimentary to the sequencing probe associated with the transistor.

The output from each sensor chip 2304 may be fed into a data acquisition module (DAQ) 2315. The DAQ 2215 may serve the same purpose as the external amp meter, voltmeter, or multi-meter discussed above with regards to the electrical connector in FIG. 22. The DAQ 2215 may include a multiplexer module (MUX) 2322. The MUX enables analysis of multiple samples to occur using a single DNA sequencing device 2300 by allowing a user to select which of the samples to analyze by selecting the specific open-air well 2302 and sensor chip 2304 combination. In some embodiments, the DAQ may include a current module 2324 and a voltage module 2328. The current module 2324 may be configured to identify the change in current over time based on the output signal of one of the sensor chips 2304. The voltage module may be configured to identify the change in voltage over time based on the output signal of one of the sensor chips 2304. In various embodiments, the current module 2324 and the voltage module 2328 may convert the analog signals received from the sensor chips 2304 into digital signals for processing. In some embodiments, the DAQ may include an output module 2326 to combine the output from the current module 2324 and the voltage module 2328 and output the data to a digital I/O module 2332 embodied in the processing section 2330. In some embodiments, the output module 2326 may convert the output from the current module 2324 and the voltage module 2328 into digital signals. In some embodiments, the MUX 2322 of the DAQ 2315 may also communicate with the digital I/O module 2332.

In addition to the digital I/O module 2332, the processing section may include a processing module 2334 and an interface module 2336. The digital I/O module 2332 may provide a connection between the DAQ 2315 and the processing module 2334. The processing module may be configured to process the received digital signals from the digital I/O module 2332. In some embodiments, the processing module 2334 may be configured to determine the transconductance of the sensor chip 2304 for the sample being analyzed. In other embodiments, the processing module 2334 may be configured to determine the resistance of the sensor chip 2304. In some embodiments, the processing module 2334 may be configured to identify a DNA sequence present in a suspension based on the changes in the electrical properties of a transistor with an associated sequencing protein. The change in electrical properties indicates the presence of DNA binding, indicating that the complimentary nucleotide sequence to the particular sequencing protein is in the suspension. In some embodiments, the processing module 2334 may be configured to plot the change in pH over time against one or more of the change in current, voltage, transconductance, and resistance. In some embodiments, the processing module 2334 may include a memory configured to store the instructions relevant to each of the above described processing functions for the processing module 2334.

The interface module 2336 may be configured to output the data from the processing module 2336 to the user. In some embodiments, the interface module 2336 may include a connector configured to connect with a computing device. For example, in some embodiments, the interface module may include a USB connector, a VGA connector, a parallel port connector, or some other connector configured to transmit data to a computing device. In other embodiments, the interface module 2336 may include components for wireless transmission of data, such as Wi-Fi or Bluetooth. The user may control and interact with the DNA sequencing device 2300 through the interface module 2336.

In various embodiments, the processing section 2330 may be included on the same circuit board as the sensing section 2320. In other embodiments, the sensing section 2320 may be embodied on a first circuit board, and the processing section 2330 may be embodied on a section circuit board. In such embodiments, the sensing section 2320 circuit board may be connected to the processing section 2330 circuit board through pin headers. In other embodiments, the two boards may be connected directly by disposing pin headers on both boards configured to mate with each other. In other embodiments, a connecting cable may be used to connect one pin header on the sensing section 2320 with a pin header on the processing section 2330. One of ordinary skill would appreciate that any acceptable method of connecting the two circuit boards together may be utilized, depending on the design of the DNA sequencing device 2300.

Figure 24:
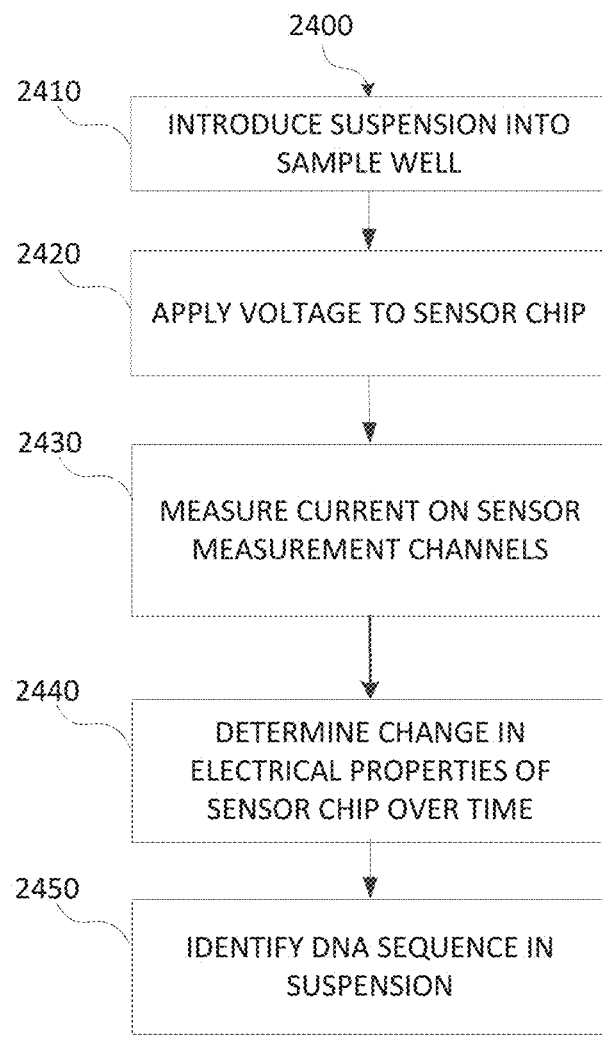
FIG. 24 is a process diagram illustrating a method for DNA sequencing consistent with embodiments disclosed herein.

FIG. 24 is a process diagram illustrating an example method of identifying DNA sequences (e.g. utilizing a DNA sequencing device). A method of identifying DNA sequences 2400 may include introducing a suspension into a sample well including a sensor chip at step 2410. The suspension may be DNA material, such as cellular material from a cotton swab, suspended in a liquid buffer as is known in the art. The sample well and sensor chip may be similar to the embodiments disclosed in FIGS. 22 and 23. Method 2400 may further include applying a voltage to the sensor chip at step 2420. In some embodiments, the voltage across the sensor chip may be held constant while the voltage across the liquid gate is varied during the measurement period. In other embodiments, the liquid gate voltage may be held constant, while the voltage across the sensor chip is varied.

In some embodiments, the voltage applied at step 2420 may be used to denature the DNA molecules within the suspension, if necessary. Method 2400 may further include measuring the current of the sensor chip on sensor measurement channels at step 2430. For example, each sensor measurement channel may be monitored through connector leads electronically coupled to corresponding transistors. In some embodiments, the method 2400 may be preceded by a calibration step, whereby solutions of known pH are introduced into the sample wells in order to determine the baseline reading for the sensor chip. Method 2400 may further include determining any change in the electrical properties of the sensor chip over time at step 2440. Changes in the transconductance and the resistance of the sensor chip indicates a release of a hydrogen ion around the sensor chip, changing the pH level. Method 2400 may further include identifying a DNA sequence of the DNA molecule in the suspension based on the change in electrical properties of the sensor chip at step 2450. The DNA sequence of a DNA molecule in a suspension is determinable by identifying the sequencing probe associated with the sensor chips in which the electrical properties changed over time, indicating a DNA binding process by the change in the pH.

The steps of measuring current on sensor measurement channels 2430, determine change in electrical properties over time 2440, and identifying the DNA sequence in the suspension 2460 may be performed by an electronic biological sample testing module. For example, a biological sample testing module may be a computer module as disclosed in FIG. 25 that includes a processor programmed with one or more computer programs configured to perform the steps disclosed herein. Other steps of method 2400 may be similarly performed by a computer module.

Figure 25:
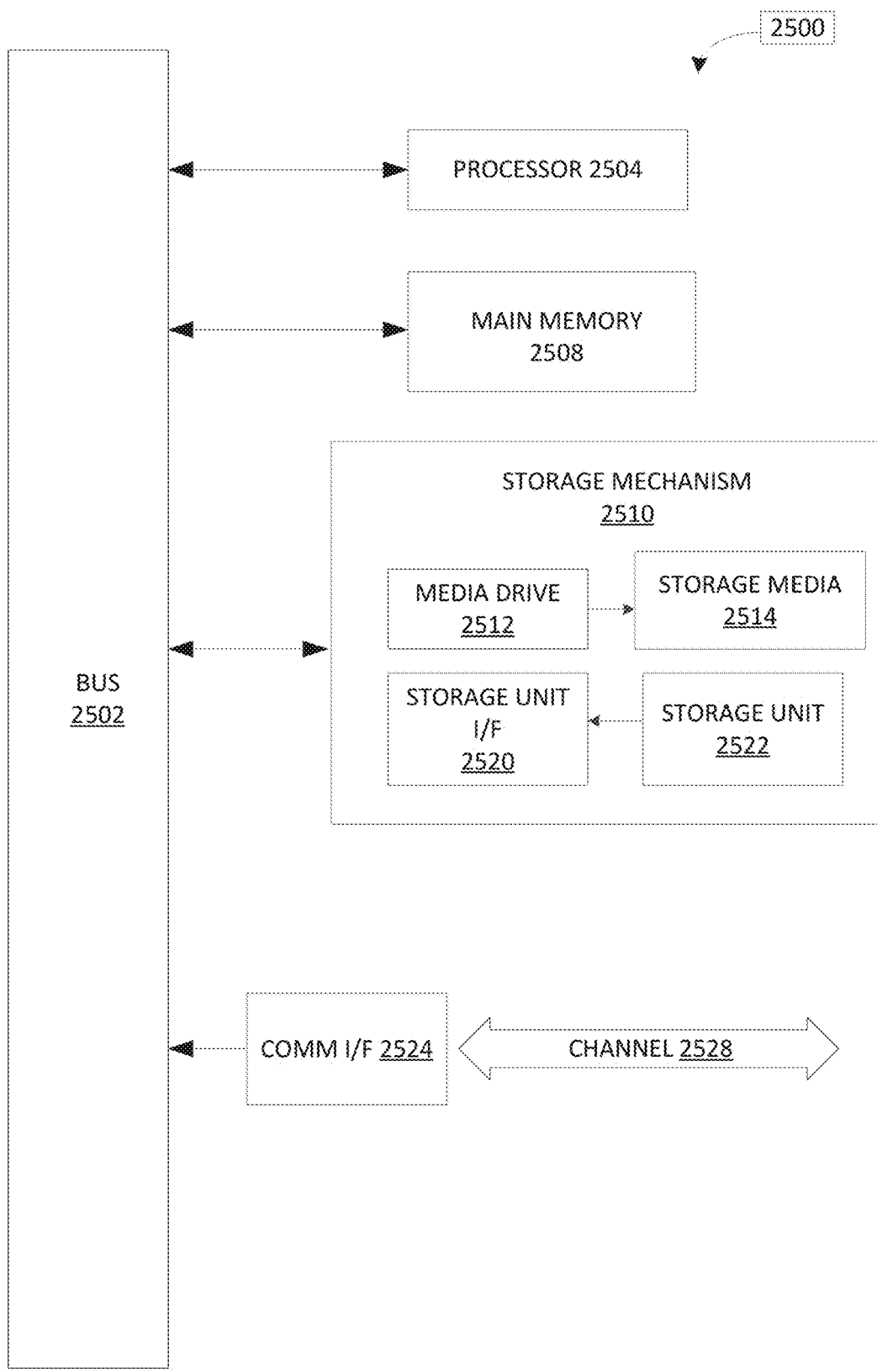
FIG. 25 illustrates an example-computing module that may be used to implement various features of the systems and methods disclosed herein.

FIG. 25 illustrates an example computing module that may be used to implement various features of the systems and methods disclosed herein. In one embodiment, the computing module includes a processor and a set of computer programs residing on the processor. The set of computer programs may be stored on a non-transitory computer readable medium having computer executable program code embodied thereon. The computer executable code may be configured to perform one or more steps of the method for electronically testing a biological sample 1900 disclosed in FIG. 19, one or more steps of the method for electronic biological sample analysis 2000 disclosed in FIG. 20, and/or one or more steps of the method for DNA sequencing 2400 disclosed in FIG. 24.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 25. Various embodiments are described in terms of this example-computing 2500. After reading this description, it will become apparent to a person skilled in the relevant art how to implement the application using other computing modules or architectures.

Referring now to FIG. 25, computing 2500 may represent, for example, computing or processing capabilities found within desktop, laptop, notebook, and tablet computers; hand-held computing devices (tablets, PDA's, smart phones, cell phones, palmtops, smart-watches, smart-glasses etc.); mainframes, supercomputers, workstations or servers; or any other type of special-purpose or general-purpose computing devices as may be desirable or appropriate for a given application or environment. Computing 2500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing 2500 might include, for example, one or more processors, controllers, control modules, or other processing devices, such as a processor 2504. Processor 2504 might be implemented using a general-purpose or special-purpose processing engine such as, for example, a microprocessor, controller, or other control logic. In the illustrated example, processor 2504 is connected to a bus 2502, although any communication medium can be used to facilitate interaction with other components of computing 2500 or to communicate externally.

Computing 2500 might also include one or more memory modules, simply referred to herein as main memory 2508. For example, preferably random access memory (RAM) or other dynamic memory, might be used for storing information and instructions to be executed by processor 2504. Main memory 2508 might also be used for storing temporary variables or other intermediate information during execution of instructions to be executed by processor 2504. Computing 2500 might likewise include a read only memory ("ROM") or other static storage device coupled to bus 2502 for storing static information and instructions for processor 2504.

The computing 2500 might also include one or more various forms of information storage mechanism 2510, which might include, for example, a media drive 2512 and a storage unit interface 2520. The media drive 2512 might include a drive or other mechanism to support fixed or removable storage media 2514. For example, a hard disk drive, a solid state drive, a magnetic tape drive, an optical disk drive, a CD or DVD drive (R or RW), or other removable or fixed media drive might be provided. Accordingly, storage media 2514 might include, for example, a hard disk, a solid state drive, magnetic tape, cartridge, optical disk, a CD or DVD, or other fixed or removable medium that is read by, written to or accessed by media drive 2512. As these examples illustrate, the storage media 2514 can include a computer usable storage medium having stored therein computer software or data.

In alternative embodiments, information storage mechanism 2510 might include other similar instrumentalities for allowing computer programs or other instructions or data to be loaded into computing 2500. Such instrumentalities might include, for example, a fixed or removable storage unit 2522 and a storage interface 2520. Examples of such storage units 2522 and storage interfaces 2520 can include a program cartridge and cartridge interface, a removable memory (for example, a flash memory or other removable memory module) and memory slot, a PCMCIA slot and card, and other fixed or removable storage units 2522 and storage interfaces 2520 that allow software and data to be transferred from the storage unit 2522 to computing 2500.

Computing 2500 might also include a communications interface 2524. Communications interface 2524 might be used to allow software and data to be transferred between computing 2500 and external devices. Examples of communications interface 2524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 2524 might typically be carried on signals, which can be electronic, electromagnetic (which includes optical) or other signals capable of being exchanged by a given communications interface 2524. These signals might be provided to communications interface 2524 via a channel 2528. This channel 2528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 2508, storage unit 2520, media 2514, and channel 2528. These and other various forms of computer program media or computer usable media may be involved in carrying one or more sequences of one or more instructions to a processing device for execution. Such instructions embodied on the medium are generally referred to as "computer program code" or a "computer program product" (which may be grouped in the form of computer programs or other groupings). When executed, such instructions might enable the computing 2500 to perform features or functions of the present application as discussed herein.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

What is claimed is:

1. A method for biological sample analysis, comprising:
introducing a liquid comprising a biological sample into a sample well, the sample well comprising a sensor;
applying a voltage to the sensor, wherein the sensor comprises a plurality of biomolecules selected from sequencing probes and antibodies and a plurality of graphene transistors comprising one or more first transistors and one or more second transistors, wherein a first biomolecule comprising a first sequencing probe is covalently bound directly or through a linker to a scattering site comprising sp3 hybridized carbon formed in a top surface of the graphene of the first transistors and a second biomolecule different from the first biomolecule is immobilized adjacent to the top surface of the graphene of one or more second transistors by an immobilization layer disposed directly on the top surface of the second transistors instead of being covalently bound thereto directly or through a linker;
identifying DNA or RNA in the liquid by measuring changes in a vector comprising a liquid gate voltage, an output current, and a slope of the transconductance of the respective first and second transistors, the changes indicating a binding event between one or more components of the biological sample selected from DNA, RNA, and antibodies, in the liquid to the first biomolecules that are covalently bound directly or through a linker to the graphene of the first transistors, or indicating a binding event between the one or more components and the second biomolecules that instead of being covalently bound directly or through a linker are immobilized adjacent to the graphene of the second transistors by an immobilization layer on top of the graphene of the second transistors.

2. The method of claim 1, wherein applying a voltage to the sensor comprises applying a drain-source voltage and a gate-source bias to the liquid.

3. A system for biological sample analysis comprising:
a sensing section including a sensor chip comprising a plurality of graphene transistors comprising first transistors and second transistors and a plurality of sequencing probes, the sensor chip including a top surface and a bottom surface;
a plate section including one or more biological sample wells configured to receive a sample liquid, each well having one or more of the plurality of graphene transistors configured to measure a vector of electrical characteristics for identifying DNA or RNA sequences in the liquid;
a processing section including a processing module configured to measure changes in the vector comprising a liquid gate voltage, an output current, and a slope of the transconductance of the graphene transistors, the changes indicating a binding event between sequencing probes associated with the graphene transistors and the DNA or RNA sequences in the sample liquid that are complementary to the respective sequencing probes;
wherein at least one of the first transistors comprises a scattering site comprising Carbon that is sp3 hybridized formed in the top surface of the sensor chip;
wherein a first sequencing probe of the plurality of sequencing probes is covalently bonded directly or through a linker to the scattering site of the first transistors; and
wherein a second sequencing probe of the plurality of sequencing probes for detecting a different nucleotide sequence from that of the first sequencing probe is immobilized adjacent to the top surface of the graphene of the second transistors by an immobilization layer disposed on a top surface of the graphene of the second transistors instead of being covalently bonded, directly or through a linker, to a scattering site on a top surface of the graphene of the second transistors.

4. The system of claim 3, wherein the sensing section is embodied on a first circuit board, the processing section is embodied on a second circuit board, and the first circuit board is in data communication with the second circuit board.

5. The system of claim 3, wherein the processing module is configured to identify DNA or RNA in the with nucleotide sequences complementary to the respective sequencing probes.

6. The system of claim 3, the processing section further comprising an interface module, wherein the interface module outputs data processed by the processing module.

7. The system of claim 3, the processing section further comprising an interface module, wherein the interface module enables a user to control the system.

8. The system of claim 3, the sensing section further comprising a data acquisition module, wherein the data acquisition module converts analog signals from the sensor chip into digital signals.

9. The system of claim 3, wherein the immobilization layer comprises a hydrogel.

10. The system of claim 3, wherein the immobilization layer comprises a non-hydrogel adherent.

11. An apparatus comprising:
a sensor chip comprising a plurality of transistors comprising one or more first transistors and one or more second transistors and individually comprising a graphene surface for sensing changes in transistor current versus liquid gate voltage and configured to communicate an output signal to a processing module in response to detecting one or more predetermined components comprising first components and second components of a biological sample in a liquid dispensed on the sensor chip;
wherein the sensor chip is configured to detect the first components of a biological sample using a first biomolecule covalently bonded directly or through a linker to a scattering site comprising sp3 hybridized carbon formed in a top surface of graphene of the first transistors; and
wherein the sensor chip is further configured to detect the second components of the biological sample using a second biomolecule that, instead of being covalently bound directly or through a linker to the graphene, is immobilized adjacent to the graphene of the one or more second transistors by an immobilization layer disposed on to a top surface of graphene of the one or more second transistors.

12. The apparatus of claim 11, wherein the immobilization layer comprises a hydrogel.

13. The apparatus of claim 11, wherein the immobilization layer comprises a non-hydrogel adherent.

14. The apparatus of claim 11, wherein the sensor chip is configured to identify the first biological components and the second biological components of the biological sample in the sample liquid based on changes to values of a measurement vector comprising output current of the transistor, liquid gate voltage, and slope indicating transconductance of the transistors, the changes in response to binding of first and second nucleotide sequences to complementary sequencing probes associated respectively to the first or second transistors.

15. The apparatus of claim 11, wherein the plurality of transistors are arranged into groups of transistors comprising at least a first group of transistors and a second group of transistors.

16. The apparatus of claim 15, wherein the first group of transistors and the second group of transistors each comprise five or more transistors configured in a linear arrangement.

17. The apparatus of claim 16, wherein a reference electrode is horizontally disposed on a surface of the sensor chip between the first group of transistors and the second group of transistors.

18. The apparatus of claim 17, wherein the reference electrodes are used to bias and/or measure the liquid gate voltage of the liquid covering the first group of transistors and the liquid covering the second group of transistors.

19. The apparatus of claim 15, wherein the apparatus is configured to analyze multiple drops of sample liquid using a first drop of sample liquid with a sufficiently small volume so as to limit an area of the first drop to the area above the first group of transistors and using a second drop of sample liquid with a sufficiently small volume so as to limit an area of the second drop to the area above the second group of transistors.

20. The apparatus of claim 15, wherein the first biological components comprise antibodies and the second biological components comprise nucleotide sequences from DNA or RNA.

* * * * *